United States Patent [19]

Fields et al.

[11] 4,255,537

[45] Mar. 10, 1981

[54] POLYMERIC IMMUNOREGULATORY AGENTS CONTAINING HALF-AMIDE/HALF CARBOXY/IMIDE GROUPS

[75] Inventors: Joseph E. Fields, Ballwin; Samuel S. Asculai, St. Louis; John H. Johnson, Kirkwood, all of Mo.

[73] Assignee: Monsanto Company, St. Louis, Mo.

[21] Appl. No.: 5,638

[22] Filed: Jan. 22, 1979

[51] Int. Cl.³ .............................................. C08F 8/30
[52] U.S. Cl. .................................. 525/328; 525/378; 528/322; 528/335
[58] Field of Search ............... 525/328, 378; 528/335, 528/345, 322

[56] References Cited

U.S. PATENT DOCUMENTS

| | | | |
|---|---|---|---|
| 2,883,287 | 4/1959 | Kosmin et a. | 525/328 |
| 3,157,595 | 11/1964 | Johnson et al. | 210/54 |

FOREIGN PATENT DOCUMENTS 664326  4/1963  Canada .

OTHER PUBLICATIONS

Advances in Cancer Research-Regelson, vol. 11, (1968), pp. 223-226, 240-241.
Nature-Regelson et al., vol. 186, (1960), pp. 778-780.
Polymeric Science and Technology-Regelson, vol. 2, (1973), pp. 161-168.
Pure and Applied Chemistry-Breslow, vol. 46, (1976), pp. 103-113.

*Primary Examiner*—Harold D. Anderson
*Attorney, Agent, or Firm*—Scott J. Meyer; James W. Williams, Jr.

[57] ABSTRACT

The disclosure relates to copolymers of olefin monomers having from 2 to about 4 carbon atoms and $\alpha,\beta$-unsaturated polycarboxylic anhydrides having from 4 to about 6 carbon atoms, having an average molecular weight of from about 300 to about 1500, and derivatized to contain both a half-amide, half-carboxylate salt function and an imide function in which said imide function comprises from about 5% to about 40% of said derivatized function.

The utility of these copolymers in the management of tumor therapy to prevent tumor recurrence or development of metastases by an immunoregulatory mechanism has been demonstrated in rats and mice.

11 Claims, 3 Drawing Figures

POLYMERIC IMMUNOREGULATORY AGENTS CONTAINING HALF-AMIDE/HALF CARBOXY/IMIDE GROUPS

BACKGROUND OF THE INVENTION

This invention relates to polymeric compounds which have been demonstrated in rats and mice to have utility in the immunoregulatory management of tumor therapy.

Although the field of tumor therapy has been the subject of extensive study, very few effective compounds for such use have been found so far.

According to one approach, attempts are made to manipulate the body's immune system. For example, it is generally recognized that the thymus gland is of great importance in the development and senescence of immunological competence. By various mechanisms believed to be principally hormonal, the thymus gland exerts control over the T-lymphocyte mediated immune function. A variety of naturally-occurring and synthetically prepared peptides have thus been tested as stimulants and/or suppresants of this immune system with varying results.

Other agents that have been found to have immune adjuvant activity include, for example, Bacillus Calmette-Guerin (BCG), Corynebacterium parvum, glucan, levamisole and tilorone. Some of these compounds increase the production of antibodies while others either enhance or inhibit cell-mediated immunity.

Various biologically active synthetic polyelectrolytes also have been proposed as useful antitumor agents. Thus, Regelson and Holland found a wide spectrum of antitumor activity in mice for the sodium salt of polyethylenesulfonate. *Nature* (London) 181, 46 (1958). A number of carboxylic acid polymers of substantially high molecular weight, for example, polyacrylic acid, polymethacrylic acid, and ethylenemaleic anhydride copolymer (EMA) were then found to have antineoplastic activity similar to that of sodium polyethylenesulfonate. Regelson et al., *Nature* (London) 186, 778-80 (1960); Regelson, "Water-Soluble Polymers", in "Polymer Science and Technology", Vol. 2 (ed. N. K. Bikales), pp. 161-77, Plenum Press, New York, 1973. The antineoplastic activity of the EMA type polymers also is disclosed in Canadian Pat. No. 664,326, corresponding to U.S. Application Ser. No. 758,023, filed Oct. 28, 1958, now abandoned. The useful molecular weight of these polymers is said to range between 500 and 1.5 million. One of these polymers, the half-amide, half-ammonium salt of EMA having an average molecular weight of 20,000-30,000, was later reported to be chronically toxic in rodents and dogs. Mihich et al., *Fed. Proceedings*, Vol. 19, No. 1, Pt. 1, March 1960. Chronic toxicity also was later reported with the 2000-3000 molecular weight polymer in dogs by Mihich et al. *Fed. Proceedings*, Vol. 20, No. 1, Pt. 1, March 1961. These findings of toxicity militated against clinical testing of the polymers.

Subsequently, the related 1:2 divinyl ether-maleic anhydride copolymer showed antitumor activity in tests conducted by the National Cancer Institute. Breslow, *Pure & Appl. Chem.* 46, 103-13 (1976). This copolymer also is known as pyran copolymer or DIVEMA, and one well-known sample has been designated NSC 46015. The use of these pyran copolymers as anti-tumor agents also is disclosed in U.S. Pat. Nos. 3,224,943 and 3,794,622, wherein the useful molecular weight is described as ranging from 5000-30,000. The antitumor activity of pyran copolymer has been attributed to an immunopotentiation or to an effect upon the immune response through the recticuloendothelial system (RES) by enhancing macrophage function in a number of papers which include, for example, Breslow, *Pure & Appl. Chem.* 46, 103-13 (1976); Mohr et al., *Prog. Cancer Res. Ther.* 7, 415-26 (1978); Schultz et al., id. 7, 459-67 (1978); and Dean et al, *Cancer Treatment Reports* 62, September 1978.

DESCRIPTION OF THE INVENTION

Notwithstanding the prior reported chronic toxicity of various of the higher molecular weight EMA type polymers, research investigation was carried out by the present inventors to further evaluate polymers of that general type for immunoregulatory activity. New approaches and new methods of evaluation were instituted which allowed the recognition of immunoregulatory activity without attendant cytotoxicity. As a result, certain of these more recently evaluated compounds were found to have no direct cytotoxic activity, yet surprisingly and unexpectedly were found to be very effective against tumor metastases and tumor recurrence in rats and mice after excision or removal of bulk tumor. Thus, these compounds are indicated as particularly useful in the management of tumor therapy by an immunological mechanism. They are useful to prevent tumor recurrence or development of metastases by administration after excision or removal of bulk tumor by surgery, X-ray or cytotoxic chemotherapy.

In accordance with the present invention, a new group of compounds of the aforesaid EMA general type have been synthesized which have been demonstrated to have utility against tumor metastases and tumor recurrence in rats and mice even though lacking strong primary antitumor activity. These compounds are copolymers of olefin monomers having from 2 to about 4 carbon atoms and $\alpha,\beta$-unsaturated polycarboxylic anhydrides having from 4 to about 6 carbon atoms, having an average molecular weight of from about 300 to about 1,500, and derivatized to contain both a half-amide, half-carboxylate salt function and an imide function in which said imide function comprises from about 5% to about 40% of said derivatized function. Illustrative examples of such olefin monomers are ethylene, propylene and isobutylene; illustrative examples of such polycarboxylic anhydrides are maleic anhydride, citraconic anhydride and aconitic anhydride. Of these monomeric components ethylene and maleic anhydride are preferred.

For purposes of illustration and not limitation, the preferred copolymer of ethylene and maleic anhydride as appropriately derivatized can be represented as having the following structural units or groups:

(a) half-amide, half-carboxylate salt

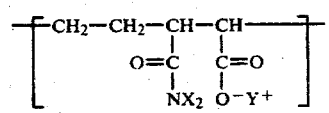

and (b) imide

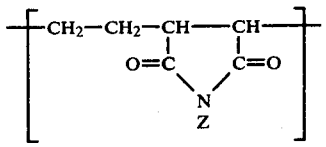

wherein

X=H or C$_{1-4}$ alkyl, and preferably H;

Y=H, ammonium or a pharmaceutically acceptable metal cation, and preferably ammonium; and Z=H, C$_{1-4}$ alkyl, ammonium or a pharmaceutically acceptable metal cation, and preferably H.

The respective (a) and (b) units or groups are distributed along a substantially linear continuous carbon atom molecule. From about 5% to about 40% of these units should be imide with the balance being principally half-amide, half-carboxylate salt units. These units can be positioned randomly within the chain and/or randomly within the polymer. It will be appreciated that a small portion (believed to be less than 10%) of monoammonium carboxyl or other pharmaceutically acceptable salt group and/or dicarboxyl group also can be present as may arise from partially reacted or unreacted anhydride during the preparation of these compounds.

Of the foregoing derivatized groups, the (a) half-amide, half-carboxylate salt group preferably is half-amide, half-ammonium salt, and the (b) imide group preferably is unsubstituted imide.

Again, for purposes of illustration and not limitation, the preferred copolymer of ethylene and maleic anhydride as preferably derivatized can be represented as having the following structural units or groups:

(a) half-amide, half-ammonium salt

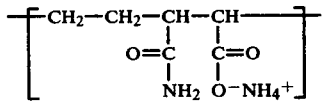

and (b) unsubstituted imide

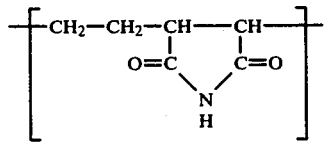

As before, the respective (a) and (b) units or groups are distributed along a substantially linear continuous carbon atom molecule. From about 5% to about 40% of these units are preferably unsubstituted imide with the balance being principally the preferred half-imide, half-ammonium salt units. These units can be positioned randomly within the chain or randomly within the polymer. It will be appreciated that a small portion (believed to be less than 10%) of monoammonium carboxyl or dicarboxyl group can be present as may derive from partially reacted or unreacted anhydride during the preparation of these compounds.

The polymeric immunoregulatory agents of this invention also preferably are water soluble.

The invention is further illustrated by the accompanying drawings in which.

Figure 1:
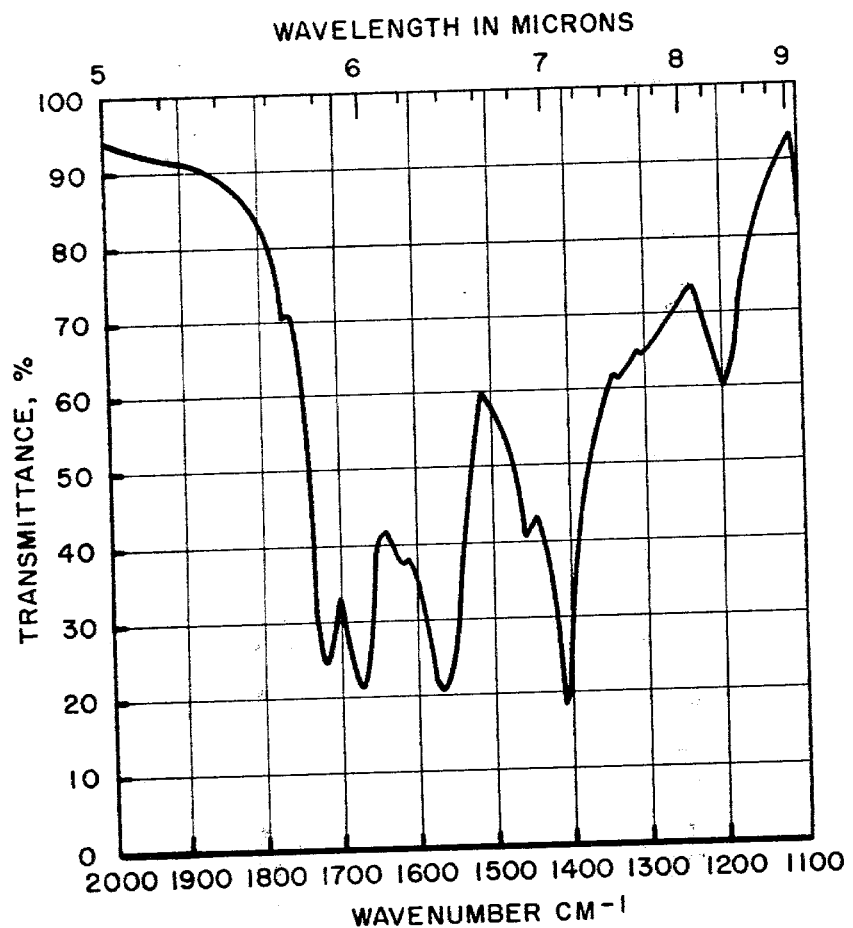
FIG. 1 shows the fingerprint region of the infrared absorption spectrum of a representative polymer of this invention which is derivatized to contain 20% imide. See Example 3, Table IV, Run 5, below.

Although Canadian Pat. No. 664,326 discloses the use of the half-amide, half-ammonium salts of EMA type copolymers, or the use of imides or partially imidized derivatives of EMA type copolymers for antineoplastic activity, it is believed that the specific polymers of this invention having the combination of both (a) the half-amide, half-carboxylate salt function and (b) the imide function in the proportions defined herein and having a relatively low average molecular weight of from about 300 to about 1500 are novel. These new polymers have unobvious, useful immunoregulatory properties which are not exhibited by the corresponding polymers having only the (a) or the (b) function or having substantially higher molecular weight. Also by way of comparison, the corresponding monomeric fragments of these polymers, namely succinimide and succinamic acid (ammoniated succinic anhydride) previously were described as not showing any significant tumor inhibiting effectiveness, Regelson et al., *Nature* (London) 186, 778–80 (1960).

The underivatized low molecular weight copolymers which are used to prepare the desired immunoregulatory agents of this invention can be prepared by well known methods as described, for example, in U.S. Pat. Nos. 2,857,365; 2,913,437; 2,938,016; and 2,980,653. Typically, the olefin, for example ethylene, is reacted with the polycarboxylic anhydride, for example maleic anhydride, at temperatures ranging from about 40° C. to about 100° C. in the presence of a free-radical promoting catalyst and a liquid solvent that is a solvent for the reactants and a nonsolvent for the interpolymer formed. Conventional peroxide type and azo type free-radical promoting polymerization catalysts are eminently suitable for this purpose, and benzoyl peroxide, for example, is preferred. Inert solvents such as benzene, halobenzenes, and haloparaffins are useful solvents for the polymerization reaction. However, an alkylated aromatic hydrocarbon having at least one α-hydrogen, such as for example ethyl benzene, isopropyl benzene, diisopropyl benzene, toluene, or xylene, is a preferred liquid medium for the polymerization reaction for the purpose of reducing the molecular weight of the copolymer product as described in U.S. Pat. No. 2,913,437. Ethyl benzene is especially preferred as the liquid medium for the latter purpose. The copolymer preferably contains substantially equimolar quantities of the olefin residue and the anhydride residue such as will be obtained by the use of about equimolar quantities of the reactant monomers. The resulting copolymer product is obtained in solid form and is easily recovered by filtration, centrifugation and the like separation procedures.

It will be appreciated that the free-radical initiator, both through initiation of the polymerization reaction and subsequent termination or telomerization with the alkylated aromatic hydrocarbon liquid medium, will cause the introduction of various organic moieties into the polymeric structure. The percentage of these moieties in the total polymer composition will increase as the molecular weight of the polymer is decreased. For example, use of benzoyl peroxide as the free-radical initiator and ethyl benzene as the liquid reaction medium will cause introduction of their respective aromatic moieties into the polymeric structure. These moieties will constitute a higher percentage of the total structure of the polymers having about 300 molecular weight than the polymers having about 1500 molecular weight.

It will be further recognized that in the preparation of these low molecular weight copolymers a certain amount of cross-linking agent can be incorporated into the copolymer to thereby render the product insoluble in water. Examples of such cross-linking agents are vinyl and allyl esters, especially the acrylates and crotonates as described in U.S. Pat. No. 3,165,486. The copolymers also can be insolubilized after derivatization, by various means such as, for example, cross-linking with diamine as described in U.S. Pat. No. 3,554,985, or by attachment to carriers such as bentonite, latex particles, or erythrocytes.

It is known that amide derivatives of the EMA type copolymers can be prepared by reacting the copolymer with ammonia gas at ordinary or elevated temperatures as described in Canadian Pat. No. 664,326 and in U.S. Pat. Nos. 2,883,287 and 3,157,595. It is also known that reaction at higher temperatures tends to promote imide formation, while reaction in inert organic liquid solvent media such as benzene can be used to control the reaction temperature and retard imide formation. Another known method for amide formation comprises reaction of the polymer in liquid ammonia at $-33°$ C.

Figure 2:
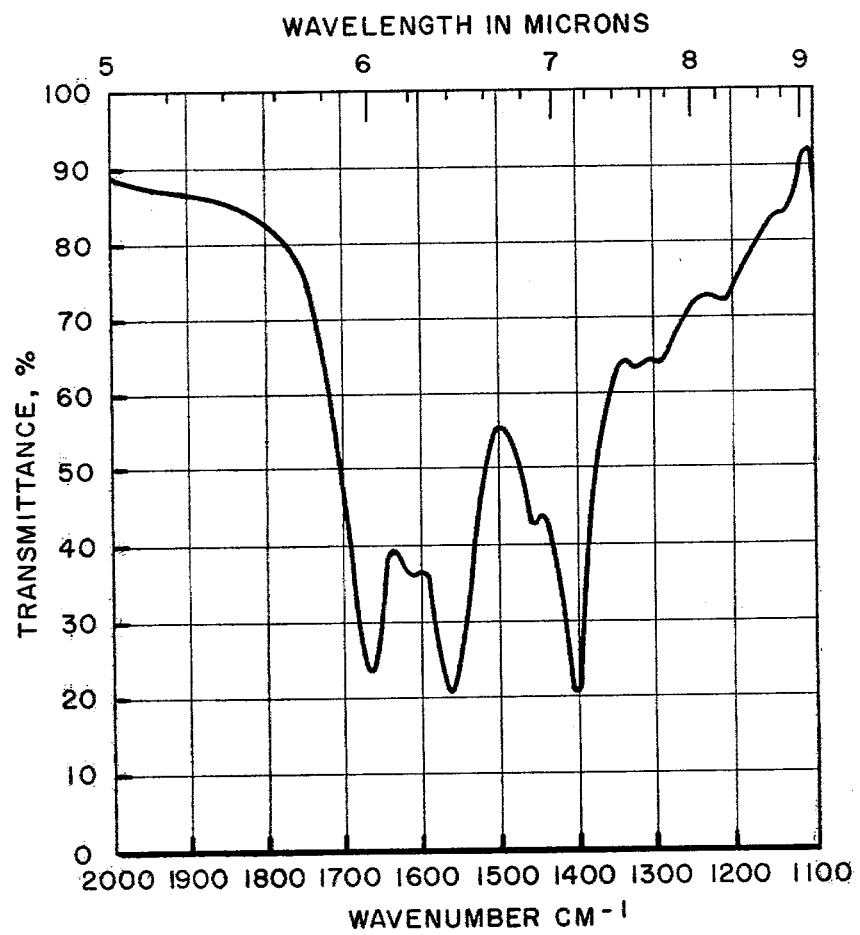
FIG. 2 shows for comparative purposes the fingerprint region of the infrared absorption spectrum of a corresponding polymer which contains 0% imide. See Example 2(a) below.

While the aforesaid procedures are generally useful for preparation of the half-amide, half-ammonium salt as an intermediate step to preparation of the imide containing derivatives, they are deficient from a time-diffusion effect of ammonia into the inner core of the EMA particles for purposes of this invention as described in Example 2, below. A preferred method for purposes of the present invention comprises first dissolving the EMA type copolymer in acetone followed by reaction of the dissolved polymer with liquid ammonia in acetone. The desired half-amide, half-ammonium salt product precipitates out of solution and then can be readily recovered by filtration, centrifugation and the like separation procedures as illustrated further in Example 2, parts a, b and c, below. FIG. 2 of the accompanying drawings shows the infrared spectrum of the half-amide, half-ammonium salt product of said Example 2(a), which contains 0% imide.

Preparation of the desired imide containing derivative then can be obtained by reacting the intermediate half-amide, half-ammonium salt with ammonia in suitable organic solvent media such as, for example, toluene or xylene, at refluxing temperatures until the desired percentage of imide derivative is formed as illustrated further in Examples 3 and 4, below.

FIG. 1 of the accompanying drawings shows the infrared spectrum of a representative example (Example 3, Table IV, Run 5) of the desired polymer which is derivatized to contain both (a) the half-amide, half-ammonium salt function and (b) the imide function, and in which the imide comprises 20% of said derivatization. The polymer of this example has an average molecular weight of about 850 and the 20% imide lies within the preferred range of about 10% to about 25% imide.

Figure 3:
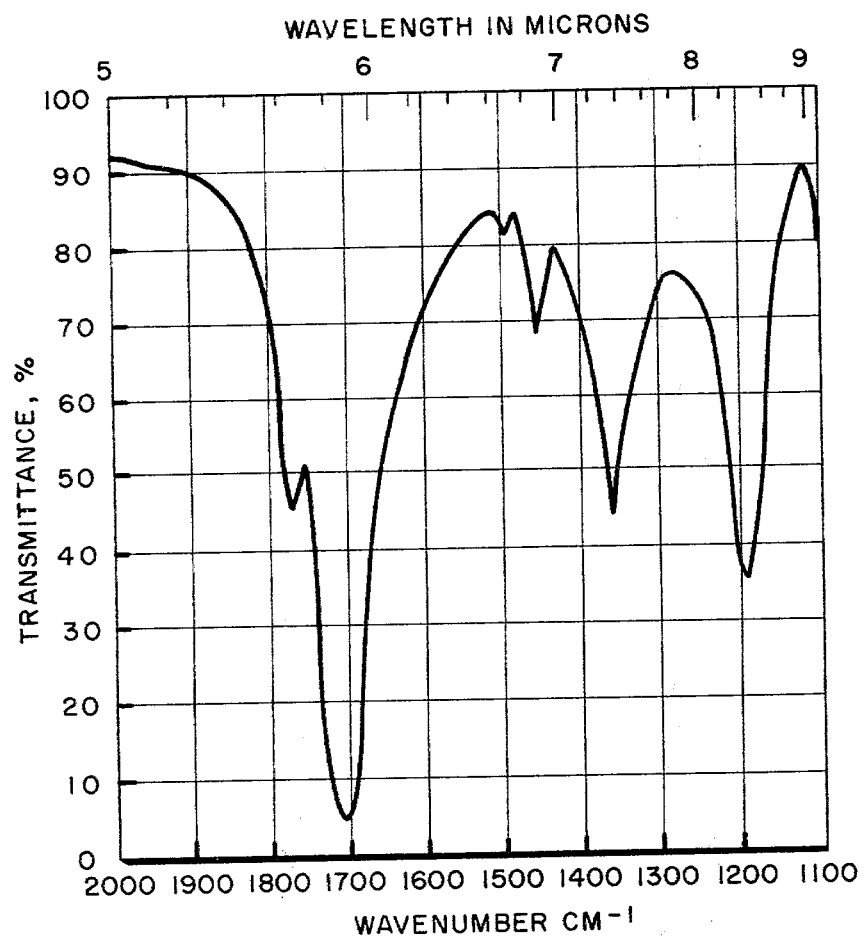
FIG. 3 shows for comparative purposes the fingerprint region of the infrared absorption spectrum of a corresponding polymer which is derivatized to contain 100% imide. See Example 5, below.

For purposes of comparison, a full 100% imide derivative of the EMA copolymer also was prepared as illustrated in Example 5, below. FIG. 3 of the drawings shows the infrared spectrum of this polymer.

A detailed description of the infrared analysis for identification of the various aforesaid functional groupings as illustrated in FIGS. 1 to 3 is set forth below, following Example 1.

In order to demonstrate the utility of polymers of this invention in the immunoregulatory management of tumor therapy, representative examples of the polymers were subjected to various tests in rats and mice as follows:

In one series of tests, the polymers were tested in a virus-induced, non-metastatic mouse tumor model. The model used was the SV40-virus induced fibrosarcoma (m KSA) of syngeneic BALB/c mouse origin. This murine tumor, mKSA-TU5, was originated by Kit et al. *Int. J. Cancer* 4, 384-392 (1969) and is not known to regress in syngeneic BALB/c mice. In this series of tests the tumor regressions observed were related to immunostimulation and reduction of tumor load in agreement with Dean et al., *Int. J. Cancer*, 16, 465-475 (1975) who demonstrated that mKSA possessed tumor associated antigens and that in small tumor bearing animals there was good correlation with cell mediated immunity. The mice were treated with three different doses of the test compound either before or after or both before and after challenge with viable tumor cells at a $TD_{100}$ and $TD_{50}$. The growth of tumors was then evaluated in the treated animals versus normal non-treated control mice. In this series of tests, polymers of this invention having an average molecular weight of about 850 showed substantially greater tumor regression activity than the corresponding polymers of 2000-3000 molecular weight and 20,000-50,000 molecular weight.

In another series of tests, representative polymers of this invention were tested in a chemically-induced, metastasizing rat tumor model. The model used was a 3-methylcholanthrene-induced bladder tumor (BLCA) in Fischer 344 rats. Prehn, R. T. et al, *J. Nat. Can. Inst.* 18, 769 (1957) and Falk, R. et al, *Surgery*, October (1978). The tumor cells had been passaged in cell culture over five years and, after subcutaneous (SC) implantation, were known to metastasize to the lungs within one week of implantation. The usual time of survival following subcutaneous tumor implantation is three weeks or less.

In one part of these tests in the metastasizing rat tumor model, the test polymer was administered periodically at about weekly intervals for three weeks following tumor implantation. These treated animals had a survival rate greater than three times that of the untreated control animals and no metastatic growth was noted during the six weeks of observation.

In another part of these tests in the metastasizing rat tumor model, the test polymer was administered as an adjunct to tumor excision at 7-10 days post tumor inoculation. The treated animals were observed for tumor recurrence after excision versus untreated control animals. In the control animals tumor recurrence was 100% within six weeks post resection with an average time of 32 days whereas in the animals treated with preferred polymers of this invention at 30 mg/kg there were no recurrences during the first six weeks and after 10 weeks tumor recurrence was seen in only 13% of the animals.

In yet another series of tests, representative polymers of this invention were tested in normal Lewis strain rats and were found to stimulate immune responses as evidenced by an increase in antibody production.

Still other tests in normal Lewis strain rats showed B-cell activation by representative polymers of this invention without the presence of T-cells, thus indicating the use of these polymers as a thymic function replacement. T-cells are thymus-derived lyomphocytes while B-cells are lymphocytes which differentiate in the bursal equivalent or bone marrow.

Further testing in normal Lewis strain rats for increase in peritoneal macrophages and activity of latex phagocytosis of the macrophages has indicated that the immunoregulatory effect of these polymers on B-cell activity is not produced by stimulation of macrophage activity. The polymers of this invention thus appear to function differently than the related pyran copolymers of the prior art which act through the RES by enhancing macrophage function.

A detailed description of the aforesaid and other such tests and the corresponding results are set forth in Examples 8 to 23 below.

In general, the polymers of this invention can be administered in an effective immunoregulatory amount as an adjuct to tumor chemotherapy, tumor radiation therapy and/or tumor excision. As such adjuncts in the management of tumor therapy they can be administered at about the same time as such therapy, or within an appropriate time prior to or subsequent to such therapy. Generally, this would be within the two day period immediately preceeding and the one month period immediately following such therapy. Studies indicate that clearance of a preferred water-soluble polymer of this invention occurs in about 30–60 days and thus it is anticipated that administration of booster doses of the polymer can be provided at about every six weeks.

The polymers can be administered parenterally as well as orally in amounts ranging, for example, from about one to about 100 mg. per kg of body weight. They can be administered both intravenously and intraperitoneally, preferably in aqueous solution such as sterile water or saline. Orally, they can be administered in the form of tablets, powders, capsules, elixers and the like dosage forms in admixture with common solid and liquid diluents, carriers, suspending agents and adjuvants such as for example, cornstarch, lactose, talc, stearic acid, magnesium stearate, gelatin, acacia and locust bean gums, alcohol, water, dimethylsulfoxide (DMSO), vegetable oils and the like materials. The oral dosage form preferably is solid reconstituted in a suitable liquid mixture at the time of administration in order to maintain stability of the dual groupings of (a) half-amide, half-carboxylate salt and (b) imide. Other suitable dosages of the polymers to produce a desired immunoregulatory effect can be determined by reference to the specific examples set forth hereinafter.

Although the following detailed examples will further illustrate the invention, it will be appreciated that the invention is not limited to these specific examples.

EXAMPLE 1

Preparation of EMA

The desired raw material ethylene/maleic anhydride (EMA) copolymer was prepared in a heated one-gallon stainless steel reactor fitted with internal water cooling coil, magnetic driven stirrer operating optimally at 1000–1200 r.p.m., ethylene inlet and an inlet through which additional catalyst could be added in solution pressured in by ethylene. Samples could be withdrawn or the final contents emptied through a bottom port. Auxilliary equipment for heating and cooling control were provided. In a typical run the charge to the reactor consisted of 1625 g. (1875 ml) ethylbenzene, 190 g. (1.94 mole) maleic anhydride, and 14.1 g. (0.058 mole) benzoyl peroxide dissolved in 80 g. (92 ml) ethylbenzene. The catalyst vessel was washed into the reactor with an additional 20.0 ml ethylbenzene. The reactor was closed and pressure vented twice with ethylene at room temperature to displace air in the system. Thereafter the temperature was brought to and held at 70° C. with an ethylene feed pressure of 200 p.s.i. for the duration of the polymerization. After three hours polymerization at 70° C. and 200 p.s.i. ethylene pressure an addition of 9.4 g (0.039 mole) benzoyl peroxide in 60 g (70 ml) ethylbenzene was made through the catalyst addition line followed by a wash of this inlet with 20 ml ethylbenzene. Stirring with heating at 70° C. at 200 psi. ethylene feed was then continued for an additional 14 hours to complete the polymerization. At the end of the run the reactor was cooled and vented and the contents consisted of an ethylbenzene slurry of product ethylene/maleic anhydride (EMA) copolymer and a small amount of product EMA glazed on the stirrer, cooling coils and reactor surfaces. This slurry was filtered, after combining with the glazed material removed by scraping, and the conversion of maleic anhydride was determined on the filtrate by NaOH titration to a phenolphthalin end point.

The total EMA product workup consisted of filtration, slurry extraction three times (1 hour each) with 2 liters xylene at room temperature followed by three extractions (1 hour each) with 2 liters hexane and final filtration. Filtration was employed between all extraction steps. The final EMA product was vacuum dried overnight with full oil pump vacuum at 55°–60° C. The thus dried EMA product was pulverized in a Waring blender for 5 minutes to reduce the minor portion of glazed material to a powder consistency. Table I summarizes the results obtained on seven such consecutive EMA polymerizations.

TABLE I

| Run No. | Maleic Anhydride Conversion % | EMA Product Recovery g. | Hydrogen %[1] | Carbon %[1] | Specific Viscosity 1% DMF at 25° C.[2] | Equivalent Weight[3] |
|---|---|---|---|---|---|---|
| A | 91.5 | 185 | 4.98 | 57.34 | 0.064 | 138.5 |
| B | 98.6 | 227 | 5.03 | 58.11 | 0.068 | 139.9 |
| C | 98.3 | 223 | 5.10 | 58.15 | 0.063 | 140.0 |
| D | 98.3 | 219 | 5.04 | 58.24 | 0.066 | 139.1 |
| E | 97.9 | 223 | 5.10 | 57.59 | 0.063 | 140.6 |
| F | 97.9 | 225 | 5.12 | 58.14 | 0.061 | 141.5 |
| G | 98.6 | 224 | 5.11 | 58.05 | 0.064 | 140.1 |

[1] Average of two determinations.
[2] Substantially in accordance with ASTM D-2515-74 procedure, Ostwald viscometer.
[3] Weight in grams containing one mole unit of anhydride determined by potentiometric pH titration of aqueous solution with standard NaOH.

Molecular weight parameters were determined on the product EMA using preparation F above as a typical product. The material was vacuum dried for 24 hours at 100° C. using oil pump vacuum. Parameters were determined in dry dimethyl formamide (DMF). For preparation F the number average molecular weight ($M_n$) was determined as 852 using Vapor Pressure Osmometry in DMF at 120° C. using a Knauer VP Osmometer. The weight average molecular weight ($M_w$) was determined as 5730 using low angle laser light scattering, again in DMF, employing a Chromatix KMX-6 instrument. Intrinsic viscosity in DMF at 25° C. was measured by capillary viscometry using a Cannon Ubblehode dilution viscometer (size 75) by extrapolation of four different concentrations to zero concentration. The intrinsic viscosity of preparation F was found to be 0.0607 dl/g.

Similar determinations of $M_n$, $M_w$ and intrinsic viscosity were made in identical fashion using an EMA preparation of higher specific viscosity (0.11, 1%, DMF, 25° C.). In this case the intrinsic viscosity was found to be 0.1227 dl/g, the $M_n$ was 2,264 and the $M_w$ was 12,970.

Using the above values for two EMA products of varying specific viscosity the K and $\alpha$ constants in the standard equation, relating intrinsic viscosity ($[\eta]$) to molecular weight, $[\eta] = KM^\alpha$, were determined. The found relationships were:

$$[\eta]_{25}\cdot{}^{DMF} = 4.71 \times 10^{-4} M_n^{0.72}$$

and $$[\eta]_{25}\cdot{}^{DMF} = 3.51 \times 10^{-5} M_w^{0.86}$$

The term "average molecular weight" as used herein with respect to the disclosed and claimed copolymers of this invention is defined to mean number average molecular weight.

Identification of Functional Groups

The identifications of the various functional groupings for all of the polymeric derivative examples, both qualitative and quantitative, was accomplished by Infra-red analysis using a Beckman IR-12 Spectrophotometer. Sample preparation, absorbance frequency assignments and procedures to determine the ratio of imide groups to amide groupings followed procedures set forth in either "The Infra-red Spectra of Complex Molecules", Bellamy, John Wiley and Sons, 1960, or "Practical Infrared Spectroscopy," Cross, Butterworth, 1964.

Sample preparation, in all cases, utilized pressed discs of 2 mg polymer per 250 mg dry KBr composition with 70 mg of mixed polymer/KBr per disc. Absorbing band positions are quoted in units of wave number which are expressed in reciprocal centimeters ($cm^{-1}$), usually styled as band frequencies.

For qualitative "fingerprinting" of product composition as the the presence or absence of certain groups the following band frequency assignments are accepted and were used:

|  | Wave number ($cm^{-1}$) | Function |
|---|---|---|
| 1. 5-membered ring anhydride Doublet: | 1870–1830 minor<br>1800–1760 major | C=O stretch |
| 2. Undissociated aliphatic acid (COOH): | 1725–1700 | C=O stretch |
| 3. Polymeric imide, 5-membered ring Doublet: | 1715 major<br>1770 minor | C=O stretch |
| 4. Polymeric primary amide: Amide-I band | 1670 major<br>1620 minor | C=O stretch<br>NH deformation<br>and C—N stretch |
| 5. Carboxylate ion $CO_2^-$ | 1560–1570 | asymmetric stretch |
| 6. Methylene —$CH_2$— | 1470–1450 | C—H deformation |
| 7. Ammonium ($NH_4^+$) salt of carboxylate (Intensity depends upon cation nature) | 1405–1400 | symmetric stretch |
| 8. Polymers with a high concentration of imide groups (over 60%) also contain a doublet: in addition to those shown in 3 above. | 1180–1200 major<br>1370–1350 minor | C—N stretch |

For quantitative estimation of the imide/amide content of a polymer containing both groups, in addition to ammonium carboxylate function, a ratio of the absorbancy intensity of the major imide band at 1715 $cm^{-1}$ to the major primary amide band at 1670 $cm^{-1}$ was determined. The imide content was determined by comparing the measured ratio of imide/amide (above) to a standard curve of percent imide vs imide/amide absorbance ratio prepared from a series of infra-red tracings obtained by mixing increasing amounts of pure (about 100%) imide (described in Example 5) with polymer containing no imide or unionized COOH but with only amide and ionized carboxyl (described in Example 2) functions.

For this latter test of imide/amide ratio, care was taken to be sure that unionized carboxyl was not present at 1715 $cm^{-1}$ by first dissolving the sample in water, adjusting the pH to 10.0 with ammonium hydroxide and freeze-drying to convert any unionized COOH to ammonium carboxylate. Such procedures increase the intensity of the carboxylate bands at 1560 and 1400 $cm^{-1}$ but insure that the remaining band at 1715 $cm^{-1}$ is indeed of imide origin.

In all the following examples references to the presence or absence of functional groups and to the imide content of imide containing polymers is made on the basis of the presence or absence of the above functional band assignments and the above method for estimating quantitative imide/amide band intensity ratios.

EXAMPLE 2

Preparation of Half Amide-Half Ammonium COO$^-$ Salt of EMA

Previous methods for the ammoniation of EMA polymers (disclosed in U.S. Pat. No. 3,157,595 and Canadian Pat. No. 664,326) by either of three methods: (1) dry ammoniation with ammonia gas at ordinary temperatures by sparging ammonia into vigorously stirred dry EMA powder, (2) sparging ammonia into a stirred slurry of EMA powder in benzene or hexane, or (3) by direct addition of solid EMA powder to a stirred excess of liquid ammonia to yield the half amide-half ammonium carboxylate salt of EMA have been found to be deficient for the present use. This deficiency relates to a substantial time-diffusion effect of ammonia into the inner core of even finely ground EMA particles. Even with prlonged reaction time the thusly prepared amide-ammonium salt products always contain residual amounts of unreacted anhydride, approaching 5 wt percent, as evidenced by the presence of anhydride absorbancy bands at 1780 and 1850 cm$^{-1}$ frequencies.

The following preferred method was developed to obviate long reaction periods and poor temperature control with the formation of products which contained no anhydride function.

(a) EMA polymer from Example 1-F (80 g) was dissolved in 800 ml acetone (AR-grade) and this solution was added over a 20 minute period to a stirred solution of 100 ml liquid ammonia in 3 liters acetone at $-70°$ C. (Dry Ice-acetone bath). After the 20 minute addition period the total mixture was allowed to gradually warm to room temperature (4 hours) during which time the precipitated product color changed from an initial yellow to white. The product was filtered and successively slurried twice with 2 liters acetone followed by two slurries with 1.5 liters of 50/50 acetone/hexane. All slurry steps were for 30 minutes each. The final product was filtered and dried over night at 45° C. at 20–25 mm Hg vacuum. The dried product was dissolved in 900 ml, filtered through a 0.45 micron filter and freeze dried to yield 98.7 g of half amide-half ammonium carboxyl salt.

(b) Procedure (a) above was repeated as follows using EMA polymer from Example 1-F but with water added to the original EMA solution in acetone. The EMA (60 g) was dissolved in 500 ml acetone plus 2.32 g water and the solution was refluxed for 2 hours. The cooled acetone solution of EMA was added with stirring within a 10 min period to 2 liters acetone containing 3 moles liquid ammonia at $-60°$ C. As before the reaction slurry was allowed to warm to room temperature and worked up as above with 2 slurries in 1.5 liters acetone and one slurry with 1 liter hexane, filtered and vacuum dried at 40° C., 20–25 mm Hg overnight. The recovered freeze dried product, as described in (a), consisted of 84 g.

(c) A third preparation utilized EMA polymer from Example 1-G. 100 g (0.714 mole) EMA was refluxed for 2 hrs. in 700 ml. acetone containing 3.85 g water. The cooled acetone solution was added over a 10 minute period to a stirred solution of 3.8 liters acetone containing 60 ml liquid ammonia at $-50°$ C. After one hour at $-50°$ C. the reaction slurry was allowed to warm to room temperature (2 hours). The filtered product was slurried twice in 2 liters acetone (30 minutes each) and twice in 2 liters hexane (30 minutes each), filtered and dried overnight at 50° C. at full oil pump vacuum. The recovered dry half amide-half ammonium carboxyl salt was 115.6 g.

Analysis of the above three preparations is summarized in Table II.

TABLE II

| Preparation | a | b | c |
|---|---|---|---|
| Nitrogen, % (Avg. of 2) | 13.40 | 14.18 | 14.19 |
| Functional Composition by Infra red | | | |
| Anhydride | None | None | None |
| Undissociated COOH | None | None | None |
| Imide | None | None | None |
| Primary Amide | Major | Major | Major |
| Ionized COO$^-$ | Major | Major | Major |
| Methylene —CH$_2$— | Yes | Yes | Yes |
| —COO$^-$NH$_4{}^+$ | Major | Major | Major |

EXAMPLE 3

Preparation of Partial Imide Derivatives in Xylene

A 10 g sample of the half amide-half ammonium carboxyl salt of Example 2 was slurried in 250 ml xylene in a 1 liter flask fitted with stirrer, thermometer, water take-off trap and a gas inlet sparger for ammonia. The slurry was refluxed for a period of 12 hours while maintaining a steady flow of ammonia through the gas inlet sparger and while removing water. Aliquot samples of product slurry were removed at various times (see Table III) for assay of conversion to imide versus time. Each small sample was worked up by three consecutive slurries in 100 ml hexane, filtered and dried at 50° C., 20–25 mm Hg vacuum. pH of 2% aqueous solutions was measured both before and after further solution in water, pH adjustment to 10.0 (NH$_4$OH) and freeze drying. Infra red was obtained on all samples to establish imide to amide ratios and thus percent imide content. The results are tabulated in Table III.

TABLE III

| Time of xylene reflux at sample removal | pH-1[a] | pH-2[b] | I/A ratio[c] | Imide[d] % wt. |
|---|---|---|---|---|
| 15 min. | 6.26 | 7.20 | 0.723 | 13.8 |
| 30 min. | 6.00 | 5.86 | 0.858 | 18.5 |
| 45 min. | 5.91 | 5.76 | 0.999 | 23.3 |
| 1 hr. | 5.78 | 5.53 | 1.113 | 27.4 |
| 1.5 hr. | 5.43 | 5.43 | 1.398 | 36.8 |
| 2 hr. | 5.27 | 5.76 | 1.501 | 40.2 |
| 3 hr. | 4.94 | 5.72 | 1.821 | 50.0 |
| 4 hr. | 4.78 | 5.38 | — | — |
| 6 hr. | 4.73 | 5.76 | — | — |
| 7.5 hr. | 4.73 | 5.60 | — | — |
| 12 hr. | — | — | — | — |

[a]pH of 2% aqueous solution before pH adjustment.
[b]pH of 2% aqueous solution, adjusted to pH 10, and freeze dried.
[c]Ratio of IR band absorbance intensity at wave number 1715 cm$^{-1}$/1670 cm$^{-1}$.
[d]Obtained from standard curve of composition vs. I/A ratio.

A further set of nine individual experiments were run wherein half amide-half ammonium carboxyl salt of Example 2b was used. Each individual run was refluxed in xylene slurry for the noted time (Table IV) and worked up in total.

The dry products from hexane washing were individually dissolved in 150 ml water, pH adjusted to 10.0 with NH$_4$OH, filtered through a 0.20 micron filter and directly freeze dried in sterile serum bottles for in vivo animal evaluation. The yields and analysis of the various runs are described in Table IV.

TABLE IV

| Run No. | Reaction Time at xylene reflux | Product yield[1] g. | pH-1[a] | pH-2[b] | Nitrogen[c] % | I/A[d] ratio | Imide[e] % |
|---|---|---|---|---|---|---|---|
| 1. | 2 min. | 4.45 | 5.08 | 7.08 | 14.27 | 0.489 | 5.3 |
| 2. | 4 min. | 3.92 | 4.85 | 6.93 | 14.28 | 0.559 | 7.9 |
| 3. | 10 min. | 7.87 | 4.43 | 7.12 | 14.48 | 0.661 | 11.5 |
| 4. | 20 min. | 6.28 | 4.52 | 6.74 | 13.82 | 0.798 | 16.5 |
| 5. | 30 min. | 6.15 | 3.99 | 6.39 | 13.67 | 0.911 | 20.4 |
| 6. | 45 min. | 6.30 | 4.60 | 6.69 | 13.71 | 1.020 | 24.1 |
| 7. | 1 hr. | 6.30 | 4.70 | 6.22 | 13.80 | 1.139 | 28.2 |
| 8. | 1.5 hr. | 6.15 | 4.37 | 6.00 | 13.07 | 1.333 | 34.7 |
| 9. | 3.0 hr. | 5.90 | 4.33 | 5.81 | 12.52 | 1.828 | 50.1 |

[1]Run 1 used 5.0 g EMA derivative, 2 used 4.3 g, 3 used 10.0 g, rest used 8.0 g.
[a]pH of 2% aqueous solution before pH adjustment.
[b]pH of 2% aqueous solution, adjusted to pH 10.0 and freeze-dried.
[c]Obtained on pH adjusted freeze-dried product.
[d]See footnote (c) Table III - freeze-dried product.
[e]See footnote (d) Table III - freeze-dried product.

EXAMPLE 4

Preparation of Partial Imide Derivatives in Toluene

Partial imides of half amide-half ammonium carboxyl salt of EMA polymer were prepared essentially as in Example 3 except that imide formation rate was varied by operating at toluene reflux (110° C.) in toluene slurry instead of xylene as in Example 3.

The EMA used was from Example 1-F and the procedure used for preparation of the half amide-half ammonium salt was the same as Example 2a without added water. This product showed major IR absorption bands for primary amide, ionized carboxyl and ammonium carboxylate with no evidence of anhydride or imide. 28 g of this amide ammonium salt was slurried in one liter toluene and heated to reflux. Three aliquots were removed at 2 hours, 3.5 hours and 5 hours reflux time (end of run). The products were isolated by filtration, 3 slurres in 150 ml toluene and 3 slurries in petroleum ether and vacuum dried, 25 mm Hg. for 17 hours at room temperature. The dry products were then dissolved in 100 ml water, adjusted to pH 9.0 with NH4OH, filtered through a 0.20 micron filter and directly freeze dried in sterile serum bottles for in vivo animal evaluation. Results were obtained as follows:

| Toluene Reflux Time, hr. | Product g. | Nitrogen % | I/A[a] ratio | Imide[b] % |
|---|---|---|---|---|
| 2 | 6.15 | 13.78 | 0.531 | 6.5 |
| 3.5 | 7.73 | 13.41 | 0.600 | 9.5 |
| 5 | 9.24 | 13.82 | 0.647 | 11.0 |

[a]See footnote (c) Table III - freeze-dried product
[b]See footnote (d) Table III - freeze-dried product

EXAMPLE 5

Preparation of Full Imide of EMA

EMA Sp. Vics. =0.061

The full imide of EMA was prepared by refluxing 20 g of the product from Example 2a in 250 ml. xylene slurry for 18.5 hours under a constant flow of ammonia and by removing water of reaction in a Dean Start trap. A total of 2.7 ml of water was removed in the trap. The product was filtered, slurried with hexane three times and dried overnight, 25 mm Hg in vacuum at room temperature. The dry product weighed 13.5 g. Three grams of the product was stirred in 150 ml. water overnight, filtered, washed with water and freeze dried. The product had a nitrogen content of 9.53% and an IR scan exhibited absorption bands only at 1190, 1360, 1715 and 1770 cm$^{-1}$ wave numbers, typical of imide functionality. No amide, anhydride, ionized carboxyl or ammonium carboxylate absorption bands were evident.

The above full imide product was used in various admixtures with the non-imide containing half amide-half ammonium carboxylate salt from Example 2a to establish a master imide/amide infra red composition curve as previously described following Example 1 as follows: The noted amounts, weighted on an analytical balance, were mixed in stainless steel mixers using a Wigglebug Mixer. Infrared scans were determined on pressed discs of the above mixtures with dry KBr using 2 mg polymer mixture to 250 mg KBr. The pellet consisted of 70 mg of polymer/KBr mix per disc. The total master curve was constructed from the following mixed compositions:

| Weight Complete Imide from Example 5. mg. | Weight of Zero % Imide from Example 2a mg. | Imide/Amide absorbancy ratio |
|---|---|---|
| 3 | 97 | 0.427 |
| 6 | 94 | 0.509 |
| 10 | 90 | 0.621 |
| 20 | 80 | 0.843 |
| 30 | 70 | 1.161 |
| 40 | 60 | 1.519 |
| 50 | 50 | 1.871 |
| 60 | 40 | 2.099 |
| 70 | 30 | 2.564 |
| 80 | 20 | 3.008 |

EXAMPLE 5-A

Preparation of Full Imide of EMA

EMA sp. visc. =0.66

The full imide of EMA of higher molecular weight than that used in Example 5 was prepared using EMA of specific viscosity=0.66 (1%, DMF, 25° C.) corresponding to a molecular weight of 20–30,000. In this case the ammoniated EMA was prepared as in Example 6 (a) by sparging dry ammonia gas through a stirred powder EMA at a temperature below 70° C. The resulting half amide-half ammonium carboxyl salt of EMA (sp. visc. =0.66) powder was further heated at elevated temperature to convert the half amide to the imide by driving off water.

525 g. of the 0.66 sp. visc. EMA derived half amide-half ammonium carboxyl salt was vigorously stirred in a 3-gallon kettle, fitted with a water take-off and under a continuous flow of ammonia gas. The temperature was raised to 122° C. where water began to be trapped in the water take-off. After 1 hour the temperature reached 152° C. and 24 ml. water had been removed. Heating with stirring under ammonia flow was continued for 5 hours (total of 6 hours) with a total of 54 ml of water being obtained. After cooling, the product was a white floury powder. The N% was 11.11 against a theory of 11.20.

This higher molecular weight EMA 100% imide was tested for tumor growth inhibition at an independent testing laboratory in 1958 and exhibited no activity (See Example No. 22).

EXAMPLE 6

Preparation of Half Amide-half Ammonium COO⁻ salt of EMA by Prior Art Methods With and Without Water (a) A 500 ml 4-neck flask was fitted with a Teflon stirrer, thermometer, gas inlet sparger and gas outlet bubbler. The ammonia inlet gas was run through a flow meter to follow rate of flow only on a qualitative basis. To the flask was charged 25 g. of EMA from Example 1D and the powder was stirred at a rate of 500 rpm. The ammonia inlet flow was held at a rate to attain 70° C. starting from room temperature without the use of a heating mantle. Within 9 min. the powder temperature had reached 70° C. and ammonia flow was lowered to maintain this temperature. A temperature of 70° C. was maintained for 1 hr. 30 min. at which time ammonia was shut off and the reaction cooled under nitrogen. The yield of dry ammoniated EMA as half amide-half ammonium carboxylate was 30.8 g. The nitrogen percent was 14.01, 14.18 and a 2% aqueous solution pH was 6.07. IR scans indicated absorption bands for:

| Unreacted anhydride at 1780 and 1850 (less than 5% estimated) | | |
|---|---|---|
| Primary amide | at 1670 and 1620 | (major) |
| Carboxylate ion | at 1565 | (major) |
| NH$_4^+$ carboxylate | at 1405 | (major) |
| Imides | None | |

(b) A second ammoniation of EMA from Example 1D was made as in (a) above except that the EMA was first treated with water as described below to enhance reaction with ammonia and lower the anhydride component in the product. 25 g. EMA was stirred at 500 rpm at 40° C. (heating mantle) for 6 hours in the presence of 0.53 g (17 mol%) water which was added dropwise over the initial twenty minutes from a 1.0 ml syringe. After 6 hours the powder was cooled to room temperature and ammoniation was carried out as in (a), above, allowing the temperature to reach 70° C. in ten minutes. The total ammoniation time at 70° C. was one hour and the product was cooled under nitrogen. The yield was 31.4 g., percent nitrogen was 14.02, 13.94, and the 2% aqueous solution pH was 6.45. IR scans indicated the following absorption bands:

| | |
|---|---|
| Unreacted anhydride | present but much less than in (a) |
| Primary amide | Major as in (a) |
| Carboxyl ion | with NH$_4^+$ carboxylate |
| NH$_4^+$ carboxylate | being increased over (a) |
| Imide | absent |

EXAMPLE 7

Characterization of Products Previously Prepared Substantially as in Example 6

During the period of July 1956 through February 1960 the half amide-half ammonium carboxylate salt derivatives of several viscosity grades (different molecular weights) of EMA were made and evaluated. The viscosity grades, in terms of specific viscosity at 1.0 wt.% in DMF at 25° C., used ranged from 1.19, 0.60, 0.11 to 0.060. The estimated molecular weight ($M_n$) corresponding values were 50–60,000; 20–30,000; 2–3,000 and 1000. The first three, i.e. using EMA of 0.11, 0.60 or 1.19 were ammoniated in large Pilot Plant equipment yielding product amounts of 600-800 pounds. The lower viscosity (0.060) EMA was ammoniated in smaller laboratory equipment using 200-300 grams of EMA. The procedures are described below, followed by product characterization obtained at that time.

Pilot Plant procedure synopsis (for 1.19, 0.60 and 0.11 sp. visc. EMA):

The "ammoniation" vessel used was a jacketed stainless steel Stokes rotary dryer, Model 59AB fitted with proper means to introduce dry steam and anhydrous ammonia above the contents surface, a stirrer operating at 5.7 rpm. and a rotary valve for sealing the bottom and discharging the final product. The "full" volume of the unit was 40 cu. ft., the "working" volume was 27 cu. ft and the jacketed area was 63 sq. ft. In a typical run the ammoniator was closed at the bottom and 500-600 pounds of the appropriate viscosity EMA was charged with the stirrer running. The EMA was heated to 55° C. after which it was pre-hydrolyzed to the extent of 0.15-0.20 mols of water per mol of EMA by "above surface" addition of dry steam at the rate of 0.007 pounds of steam per pound of EMA over a 3-hr period. During this period, the temperature was maintained between 55° and 70° C. by use of cooling water in the jacket. Anhydrous gaseous ammonia was then admitted to the reactor (above the surface of the partially hydrolyzed EMA) at a rate such that the temperature was maintained between 60° and 70° C. (about 5-8 pounds per hr.) until 2.0 mols of ammonia per mole of EMA had been added. After all ammonia was added the product was cooled to below 50° C. and dumped into storage containers.

Laboratory procedure for 0.06 sp. visc. EMA:

The starting EMA was prepared in similar fashion to that described in Example 1 except that the reactor charge consisted of 267 g maleic anhydride, 2089 ml ethylbenzene, 45.8 ml n-butyraldehyde and 13.20 g. benzoyl peroxide added all at the beginning. The ethylene pressure was maintained for 24 hr at 200 psi at 70° C. The yield of final worked up product EMA was 279 g and the specific viscosity was 0.060 at 1% in DMF at 25° C. To a 5-liter 4-neck flask was charged 249 g of 0.060 sp. visc. EMA solid powder and this was vigorously stirred for 6 hours at 45°-55° C. after the initial dropwise addition of 5.3 g water (15 mol% based on EMA) to effect partial hydrolysis. Ammoniation was started using dry anhydrous ammonia gas sparged into the vigorously stirred solid EMA powder and the temperature was maintained at 31°-32° C. for 18 hours. During this period a slow but steady uptake of ammonia was observed. The final product weighed 320 g.

Product characterization of all of the above products is described in Table V below.

TABLE V

| Identification: | D | C | B | A |
|---|---|---|---|---|
| EMA used, sp. visc.[1] | 1.19 | 0.60 | 0.11 | 0.060 |
| Molecular Weight Range: | 50–60,000* | 20–30,000* | 2300** | 1060** |
| Ammoniated Product: CRD Code: | S-24 | 334 | 333 | 337 |
| Year prepared: | 1957 | 1957 | 1956 | 1960 |
| Nitrogen % | 15.83 | 16.86 | 14.80 | 13.83 |
| Infra red characterization: | | | | |
| Date run: | — | 5/22/59 | 6/8/59 | 7/5/60 |
| Anhydride | — | Absent | Absent | Absent |
| Carboxylic acid (COOH) | — | Absent | Absent | Absent |
| Imide | — | Absent | Absent | Absent |
| Primary amide | — | Present | Present | Present |
| Carboxylate ion ($CO_3^-$) | — | Present | Present | Present |
| Ammonium carboxylate | — | Present | Present | Present |

[1] 1% DMF, 25° C.
*Estimated $M_n$ from viscosity - $M_n$ curve relationship.
**Determined December, 1960 by the ebulliometric method, boiling point raise in acetone.

Samples of the half amide-half ammonium carboxylate salts of EMA prepared in 1957–1960 and characterized at that time as described in Table V were stored in glass jars with ordinary screw caps (not under nitrogen nor sealed in any way) until early 1977 in a general purpose warehouse. At this time (1977) they were removed for continued evaluation (see Examples 9 and 10). Before reuse the materials were recharacterized with results shown in Table VI.

It is evident that the polymer products tested in 1959–1960 (Example 8) which contained no imide at that time, had lost both ammonia and water and were thereby converted to imide-containing polymer products during the long storage period. These converted products as more recently tested in Examples 9 and 10 gave unexpectedly different results as compared to the earlier results.

TABLE VI

| Ammoniated Product | | | | |
|---|---|---|---|---|
| Identification Code: | S-24 | 334 | 333 | 337 |
| Correspondence to Table V | D | C | B | A |
| Nitrogen, % | 14.02 | 12.46 | 12.53 | 12.62 |
| Infra-red characterization: | | | | |
| Date run: | 1977 | 1978 | 1977 | 1977 |
| Anhydride | Absent | Absent | Absent | Absent |
| Carboxylic Acid (COOH) | Absent | Absent | Absent | Absent |
| Imide | Present | Present | Present | Present |
| Primary Amide | Present | Present | Present | Present |
| Carboxylate ion ($CO_2^-$) | Present | Present | Present | Present |
| Ammonium carboxylate | Present | Present | Present | Present |
| Imide/Amide Absorbance ratio | 0.890 | 0.922 | 1.180 | 0.950 |
| Imide, % | 19.5 | 20.7 | 29.5 | 21.7 |

PRODUCT EVALUATION EXAMPLES 8–21

EXAMPLE 8

Three molecular weight versions of EMA half amide-half ammonium carboxylate derivatives (containing no imide function) as identified in Example 7-V-A, B and C were evaluated at an independent testing laboratory during 1959 and 1960 using official procedures for solid Sarcoma-180 transplants as specified by the Cancer Chemotherapy National Service Center (CCNSC) and obtained from the National Institutes of Health. The procedure allowed for 2 deaths in six animals as a toxic limit. Trial T/C ratios were calculated as the ratio of the mean tumor weight of treated animals to the mean tumor weight of control animals. The T/C values were calculated for a series of three experiments if the preceding experiment met allowable limits. The material was acceptable if $(T/C)_1 \times (T/C)_2 \times (T/C)_3$ is less than 0.08 following the final experiment. Experiments were continued if $(T/C)_1$ was less than 0.54 and if $(T/C)_1 \times (T/C)_2$ was less than 0.20. Animals used were specified Swiss mice (CCNSC, specification XIV), drug route was IP (specification III) and dose determination by specification XII.

The summarized data are shown in Table VII.

TABLE VII

| Compound (Table V, Example 7) | —* | A** | B | C |
|---|---|---|---|---|
| EMA specific viscosity | — | 0.060 | 0.11 | 0.60 |
| Product Code | U-1104* | CRD337** | CRD333 | CRD334 |
| Experiment 1: dose mg/kg | 500 | 500 | 375 | 60 |
| dead/total | 2/6 | 2/6 | 0/7 | 1/7 |
| $(T/C)_1$ | 0.89 | 0.45 | 0.337 | 0.180 |
| Comment | Reject | Continue | Continue | Continue |
| Experiment 2: dose mg/kg | — | 500 | 375 | 60 |
| dead/total | — | 2/6 | 1/7 | 2/6 |
| $(T/C)_2$ | — | 0.29 | 0.159 | 0.51 |
| $(T/C)_1 \times (T/C)_2$ | — | 0.13 | 0.053 | 0.093 |
| Comment | — | Continue | Continue | Continue |
| Experiment 3: dose mg/kg | — | 500 | 375 | 60 |
| dead/total | — | 1/6 | 1/6 | 1/6 |
| $(T/C)_3$ | — | 0.77 | 0.15 | 0.50 |
| $(T/C)_1 \times (T/C)_2 \times (T/C)_3$ | — | 0.10 | 0.008 | 0.046 |
| Comment | — | Reject | Accept | Accept |

*U-1104 was the ammonium salt of succinamic acid, the monomeric functional moiety of polymers A, B, and C.
**Tested twice. Second test rejected on Experiment 1 with 500 mg/kg, dead/total = 1/6 and $(T/C)_1$ = 1.39.

It was concluded that while toxicity was improving as the molecular weight became smaller, activity was lost as the size decreased towards the inactive monomeric moeity for this series of derivatives. No similar derivatives containing the partial imide function were prepared or evaluated by CCNSC procedures, or any other procedure at the above time period (1959-1960). All three polymers (A,B and C above) were rejected when evaluated by CCNSC procedures against Carcinoma 755 and Leukemia 1210.

EXAMPLE 9

The polymer compositions (A,B,D) as described in Example 7, Table VI prepared from three different specific viscosity EMA raw materials and thus of three widely varying molecular weights, were administered to BALB/c mice using three dosage schedules, (a) before (days −9 and −1) or (b) after (days 1 and 9) tumor inoculation with SV40 transformed (designated as mKSA-TU5) tumor cells, or (c) both before (days −9 and −1) and after (days 1 and 9) the tumor challenge. The compound was administered intraperitoneally (IP) at 3 doses of 62.5, 125.0 and 250.0 mg/kg, respectively. Tumor cells were inoculated at $1 \times 10^4$ cells subcutaneously (SC) in one group of animals and at $1 \times 10^3$ subcutaneously in another group of animals. The growth of tumors in the treated mice versus normal non-treated control mice was then evaluated. The date are summarized in Tables VIII-A, VIII-B and VIII-D. From Table VIII-A using polymer from Example 7-Table VI-A employing dosage schedule (a), 48% (17/36) of tumor challenged mice remained healthy and free of tumor through the 58 day observation period. On day 61, animals free of tumor were re-challenged with viable tumor cells (mKSA-TU5 at $1 \times 10^4$ SC) and 82% (14/17) remained tumor-free (i.e. immune) at 37 days post challenge.

Using dosage schedule (b) where polymer 7-Table VI-A was given after tumor challenge, 42% (15/36) remained resistant to tumor after 58 days observation. After re-challenge (day 61) with $1 \times 10^4$ viable tumor cells, 80% (12/15) remained tumor-free at 37 days post rechallenge.

Animals in dosage schedule (c) wherein polymer 7-Table VI-A was administered both before and after tumor challenge were 28% resistant (10/36) through day 58 and all of these tumor free animals were immune to the secondary tumor challenge.

TABLE VIII-A

| mKSA-TU5 Tumor | Test Compound | Dose mg/kg | Treatment Schedule | Tumor growth in Recipients @ day 58 | Tumor Free @ day 58 |
|---|---|---|---|---|---|
| $1 \times 10^{+4}$ SC | Control | — | — | 6/6 | 0 |
| $1 \times 10^{+4}$ SC | Example 7-Table VI-A Polymer | 250 | Days −9 and −1 | 6/6 | 0 |
| $1 \times 10^{+4}$ SC | " | 125 | " | 4/6 | 2 |
| $1 \times 10^{+4}$ SC | " | 62.5 | " | 2/6 | 4 |
| $1 \times 10^{+4}$ SC | " | 250 | Days +1 and +9 | 1/6 | 5 |
| $1 \times 10^{+4}$ SC | " | 125 | " | 2/6 | 4 |
| $1 \times 10^{+4}$ SC | " | 62.5 | " | 4/6 | 2 |
| $1 \times 10^{+4}$ SC | " | 250 | Days −9 and −1, +1 and +9 | 3/6 | 3 |
| $1 \times 10^{+4}$ SC | " | 125 | " | 4/6 | 2 |
| $1 \times 10^{+4}$ SC | " | 62.5 | " | 4/6 | 2 |
| $1 \times 10^{+3}$ SC | Control | — | — | 6/6 | 0 |
| $1 \times 10^{+3}$ SC | Example 7 - Table VI-A Polymer | 250 | Days −9 and −1 | 1/6 | 5 |
| $1 \times 10^{+3}$ SC | " | 125 | " | 2/6 | 4 |
| $1 \times 10^{+3}$ SC | " | 62.5 | " | 4/6 | 2 |
| $1 \times 10^{+3}$ SC | " | 250 | Days +9 and +1 | 3/6 | 3 |
| $1 \times 10^{+3}$ SC | " | 125 | " | 6/6 | 0 |
| $1 \times 10^{+3}$ SC | " | 62.5 | " | 5/6 | 1 |
| $1 \times 10^{+3}$ SC | " | 250 | Days −9 and −1, +9 and +1 | 6/6 | 0 |
| $1 \times 10^{+3}$ SC | " | 125 | " | 5/6 | 1 |
| $1 \times 10^{+3}$ SC | " | 62.5 | " | 4/6 | 2 |

TABLE VIII-B

| mKSA-TU5 Tumor Route | Test Compound | Dose mg/Kg | Treatment Schedule | Tumor growth in Recipients @ day 51 | Tumor Free @ day 51 |
|---|---|---|---|---|---|
| $1 \times 10^4$ SC | Control | — | — | 5/6 | 1 |
| $1 \times 10^4$ SC | Example 7-Table VI-B Polymer | 250 | Days −9 and −1 | 6/6 | 0 |
| $1 \times 10^4$ SC | " | 125 | " | 3/6 | 3 |
| $1 \times 10^4$ SC | " | 62.5 | " | 5/6 | 1 |
| $1 \times 10^4$ SC | " | 250 | Days +1 and +9 | 5/6 | 1 |
| $1 \times 10^4$ SC | " | 125 | " | 4/6 | 2 |
| $1 \times 10^4$ SC | " | 62.5 | " | 5/6 | 1 |
| $1 \times 10^4$ SC | " | 250 | Days −9 and −1, +1 and +9 | 5/6 | 1 |
| $1 \times 10^4$ SC | " | 125 | " | 5/6 | 1 |
| $1 \times 10^4$ SC | " | 62.5 | " | 6/6 | 0 |
| $1 \times 10^3$ | Not Run | | | | |

TABLE VIII-D

| mKSA-TU5 Tumor | Test Compound | Dose mg/Kg | Treatment Schedule | Tumor growth in Recipients @ day 36 | Tumor Free @ day 36 |
|---|---|---|---|---|---|
| 1 × 10^{+4} SC | Control | — | — | 6/6 | 0 |
| 1 × 10^{+4} SC | Example 7 - Table VI-D Polymer | 75 | Days −9 and −1 | 6/6 | 0 |
| 1 × 10^{+4} SC | " | 50 | " | 5/6 | 1 |
| 1 × 10^{+4} SC | " | 25 | " | 6/6 | 0 |
| 1 × 10^{+4} SC | " | 75 | Days +1 and +9 | 6/6 | 0 |
| 1 × 10^{+4} SC | " | 50 | " | 6/6 | 0 |
| 1 × ^{+4} SC | " | 25 | " | 5/6 | 1 |
| 1 × 10^{+4} SC | " | 75 | Days −9 and −1, +1 and +9 | 6/6 | 0 |
| 1 × 10^{+4} SC | " | 50 | " | 6/6 | 0 |
| 1 × 10^{+4} SC | " | 25 | " | 6/6 | 0 |
| 1 × 10^{+3} SC | Control | — | — | 6/6 | 0 |
| 1 × 10^{+3} SC | Example 7-Table VI-D Polymer | 75 | Days −9 and −1 | 6/6 | 0 |
| 1 × 10^{+3} SC | " | 50 | " | 4/6 | 2 |
| 1 × 10^{+3} SC | " | 25 | " | 5/6 | 1 |
| 1 × 10^{+3} SC | " | 75 | Days +9 and +1 | 6/6 | 0 |
| 1 × 10^{+3} SC | " | 50 | " | 6/6 | 0 |
| 1 × 10^{+3} SC | " | 25 | " | 4/6 | 2 |
| 1 × 10^{+3} SC | " | 75 | Days −9 and −1, +1 and +9 | 6/6 | 0 |
| 1 × 10^{+3} SC | " | 50 | " | 5/6 | 1 |
| 1 × 10^{+3} SC | " | 25 | " | 2/6 | 4 |

Polymer from Example 7-Table VI-B was tested only in mice inoculated with 1×10^4 viable mKSA-TU5 cells (SC) (See Table VIII-B). Using dosage schedule (a) 22% (4/18) of the mice remained tumor-free throughout 51 days of observation. With schedule (b) 22% (4/18) of the tumor challenged mice likewise remained free of tumor after 51 days. In group (c) only 2/18 (11%) remained tumor-free for 51 days. On day 54 all of the above tumor free mice (10/54) were rechallenged with 1×10^4 viable mKSA-TU5 cells SC, and after 37 days all 10 remained tumor-free (i.e., immune) to tumor rechallenge.

Polymer from Example 7-Table VI-D was tested at two tumor challenge levels as with polymer 7-VI-A above (See Table VIII-D). Being much higher in molecular weight than polymers from Example 7A or 7B, the dose for polymer 7D was given (IP) at 75, 50 or 25 mg/kg as noted. With treatment schedule (a) 11% (4/36) of tumor challenged mice remained tumor-free after 36 days of observation. Of these 75% (¾) remained tumor-free after 37 days of secondary tumor rechallenge. In schedule (b) 8% (3/36) remained tumor-free after 36 days primary tumor challenge and only one of these was immune to secondary tumor rechallenge. In schedule (c) where polymer 7-VI-D was given both before and after tumor, 14% (5/36) remained tumor-free for 36 days and 4 of these 5 (80%) were immune to secondary tumor rechallenge.

The total numbers of tumor-free animals in Tables VIII A, B and D at the end of the respective observation periods derived from two sources, (a) those which were tumor-free throughout the observation period and (b) those which developed measurable tumors during the observation period and which subsequently regressed and disappeared prior to the end of the observation period.

A breakdown of regressed tumors vs. those which remained tumor-free throughout without regression indicated both a dependance on tumor load and upon the polymer used. The breakdown summary of regressed tumors from the total number of tumor-free animals is shown in Table VIII-E.

TABLE VIII-E

| Data from Table No. | Polymer | Tumor Dose Load | Tumor Free throughout[1] | Regressed Tumors[2] | Total | % Regressed |
|---|---|---|---|---|---|---|
| VIII-A | Example 7 - Table VI-A | 1 × 10^3 | 8 | 10 | 18 | 56 |
| | | 1 × 10^4 | 0 | 24 | 24 | 100 |
| | | Total | 8 | 34 | 42 | 81 |
| VIII-B | Example 7 - Table VI-B | 1 × 10^3 | NT[3] | NT | NT | NT |
| | | 1 × 10^4 | 1 | 9 | 10 | 90 |
| | | Total | 1 | 9 | 10 | 90 |
| VIII-D | Example 7 - Table VI-D | 1 × 10^3 | 10 | 0 | 10 | 0 |
| | | 1 × 10^4 | 0 | 2 | 2 | 100 |
| | | Total | 10 | 2 | 12 | 17 |

[1]Tumor free throughout observation period - not regressed.
[2]Developed tumors which regressed to zero by end of observation period.
[3]Not tested.

EXAMPLE 10

The polymer composition from Example 7-VI-A was retested as in Example 9 above except that 10 mice were used per test group and only treatment schedules (a) and (b) were employed. The data are summarized in Table IX.

Using dosage schedule (a) where polymer was given on day 9 and day 1 prior to tumor challenge, 37% (22/60) of the tumor challenged mice remained tumor-free throughout a 61 day observation period. On day 62, 21 of the tumor free animals were rechallenged with $1\times 10^4$ mKSA-TU5 tumor cells (SC) and after 30 additional days 90% (19/21) of the mice were tumor-free (immune).

In the second dosage schedule (b) where polymer was given on days 1 and 9 following tumor challenge, 47% (28/60) of the mice remained tumor free throughout the 61 day observation period. Of the 28 tumor free mice (at 61 days), 64% (18/28) remained immune for 30 additional days following secondary rechallenge with tumor.

Using treatment schedule (b) where polymer 6a was given on day 1 and day 9 following tumor inoculation, 32% (19/60) of the tumor challenged mice remained tumor-free after 61 days. Of the total 43 tumor-free mice from groups (a) plus (b) after 61 days, 36 or 87% remained immune to secondary viable tumor rechallenge ($1 \times 10^4$ cells) for a period of 30 days.

TABLE X

| mKSA-TU5 Tumor | Test Compound | Dose mg/kg | Treatment Schedule | Tumor growth in Recipients @ day 61 | Tumor Free @ day 61 |
|---|---|---|---|---|---|
| $1 \times 10^4$ SC | Control Example 6a | — | — | 9/10 | 1 |
| " | Polymer | 250 | Day −9, and −1 | 8/10 | 2 |
| " | " | 125 | " | 9/10 | 1 |
| " | " | 62 | " | 9/10 | 1 |
| " | " | 250 | Day +1, and +9 | 7/10 | 3 |
| " | " | 125 | " | 6/10 | 4 |
| " | " | 62 | " | 9/10 | 1 |
| $1 \times 10^3$ SC | Control Example 6a | — | — | 8/10 | 2 |
| " | Polymer | 250 | Day −9, and −1 | 2/10 | 8 |
| " | " | 125 | " | 5/10 | 5 |
| " | " | 62 | " | 3/10 | 7 |
| " | " | 250 | Day +1, and +9 | 7/10 | 3 |
| " | " | 125 | " | 7/10 | 3 |
| " | " | 62 | " | 5/10 | 5 |

TABLE IX

| mKSA-TU5 Tumor | Test Compound | Dose mg/kg | Treatment Schedule | Tumor growth in Recipients @ day 61 | Tumor Free @ day 61 |
|---|---|---|---|---|---|
| $1 \times 10^4$ SC | Control Example 7-VI-A | — | — | 10/10 | 0 |
| " | Polymer | 250 | Days −9 and −1 | 8/10 | 2 |
| " | " | 125 | " | 10/10 | 0 |
| " | " | 62.5 | " | 7/10 | 3 |
| " | " | 250 | Days +1 and +9 | 6/10 | 4 |
| " | " | 125 | " | 6/10 | 4 |
| " | " | 62.5 | " | 7/10 | 3 |
| $1 \times 10^3$ SC | Control Example 7-VI-A | — | — | 5/10 | 5 |
| " | Polymer | 250 | Days −9 and −1 | 7/10 | 3 |
| " | " | 125 | " | 4/10 | 6 |
| " | " | 62.5 | " | 2/10 | 8 |
| " | " | 250 | Days +1 and +9 | 7/10 | 3 |
| " | " | 125 | " | 5/10 | 5 |
| " | " | 62.5 | " | 1/10 | 9 |

EXAMPLE 11

The polymer composition from Example 6a, solid phase gaseous ammoniated EMA without added water, was administered to BALB/c mice using the dosage levels and treatment schedules of Example 10 with 10 mice per test group. Data obtained after a 61 days observation are summarized in Table X. Using treatment schedule (a) where polymer 6a was given on day 9 and day 1 prior to tumor challenge with mKSA-TU5 tumor cells, 40% (24/60) of the mice remained tumor-free after 61 days.

EXAMPLE 12

The polymer composition of Example 6b, solid phase gaseous ammoniated EMA with added water, was administered to BALB/c mice using the dosage levels and treatment schedules of Example 10 with 10 mice per test group. Data obtained after 61 days observation are summarized in Table XI. With treatment schedule (a) where polymer 6b was given on day 9 and day 1 prior to tumor challenge with mKSA-TU5 tumor cells, 30% (18/60) of the mice remained tumor-free after 61 days. With treatment schedule (b) where polymer 6b was given on day 1 and day 9 following tumor inoculation, 17% (10/60) of the tumor challenged mice remained tumor free after 61 days. Of the total 28 tumor-free mice from groups (a) plus (b) after 61 days, 23 or 82% remained tumor free for 30 days following a secondary rechallenge of $1 \times 10^4$ with tumor cells.

TABLE XI

| mKSA-TU5 Tumor | Test Compound | Dose mg/kg | Treatment Schedule | Tumor growth in Recipients @ day 61 | Tumor Free @ day 61 |
|---|---|---|---|---|---|
| $1 \times 10^4$ SC | Control | — | — | 10/10 | 0 |

TABLE XI-continued

| mKSA-TU5 Tumor | Test Compound | Dose mg/kg | Treatment Schedule | Tumor growth in Recipients @ day 61 | Tumor Free @ day 61 |
|---|---|---|---|---|---|
| " | Example 6b Polymer | 250 | Day −9, and −1 | 8/10 | 2 |
| " | " | 125 | " | 9/10 | 1 |
| " | " | 62 | " | 7/10 | 3 |
| " | " | 250 | Day +1, and +9 | 8/10 | 2 |
| " | " | 125 | " | 7/10 | 3 |
| " | " | 62 | " | 10/10 | 0 |
| 1 × 10³ SC | Control | — | — | 4/10 | 6 |
| " | Example 6b Polymer | 250 | Day −9, and −1 | 8/10 | 2 |
| " | " | 125 | " | 4/10 | 6 |
| " | " | 62 | " | 6/10 | 4 |
| " | " | 250 | Day +1, and +9 | 8/10 | 2 |
| " | " | 125 | " | 10/10 | 0 |
| " | " | 62 | " | 7/10 | 3 |

EXAMPLE 13

The evaluation described in Examples 9 through 12 were extended to a second tumor model system which was a transplantable Fischer ($F_{344}$) strain rat 3-methylcholanthrene-induced bladder carcinoma. When this tumor is transplanted into normal Fischer rats, it grows at the primary site and spontaneously metastasizes to the lung. Furthermore, recurrent cancer is always observed after surgical removal of the primary tumor.

The first study was designed to assess the effect of polymer from Example 7-VI-A on survival of rats bearing tumor and the ability of the compound to prevent formation of metastases.

Fischer strain rats, approximately 250 gm. each, were subcutaneously implanted (trochar) with a 2×2 mm section of tumor. At five, twelve and eighteen days after tumor implantation tumor-bearing rats were treated with polymer at a dose of 62 mg/kg by injection into the peritoneal cavity. In all, six animals were treated in such a fashion. Four animals with implanted tumor were left untreated and carried as controls. All of the control animals died of disease within three weeks or an average of 15 days following tumor implantation. Two of the treated animals died at 37 days. The four remaining animals were sacrificed at day 42 following implantation. Gross examination revealed that they had prominent primary tumor growth but no metastatic lung disease.

EXAMPLE 14

A second investigation was carried out to repeat Example 13 and to assess the effect of a lower dose and reduced frequency of treatment. Fischer strain rats received the same type of tumor implant and at eight days post implantation tumor-bearing rats were treated with polymer from Example 7-VI-A at 65 mg/kg or 30 mg/kg byu an I.P. injection (4 rats each group). At 16 days post implantation the lower dose group received a booster of 30 mg/kg. Survival was observed for a six week period. After six weeks, the survivors were examined for the presence of metastatic disease in their lung. Five animals with implanted tumor were untreated as controls. All of the control animals died of disease and averaged 23 days survival following tumor implantation. The group of four animals with a single dose of 65 mg/kg drug were alive at 40 days and were sacrificed. Examination revealed no metastases. Of the group which received a 30 mg/kg booster at 16 days, two died on day 35 and 36 and the remaining two were sacrificed on day 40. Again, examination revealed no evidence of metastases. Prolonged survival over control animals in both treated groups was of course self evident.

EXAMPLE 15

A third study was designed to evaluate the ability of polymer from Example 7-VI-A to prevent tumor recurrence in Fischer rats whose primary tumor was surgically removed. Fischer strain rats received a trochar implantation of a 2×2 mm section of tumor as in Examples 13, 14. The tumor was then allowed to grow to a 2–3 cm diameter size. At this stage (8 days after implantation) the tumor was removed surgically and concurrently the rat was treated with a single dose of polymer at 65 mg/kg or 30 mg/kg by an I.P. injection into two groups of four rats each. Survival and tumor recurrence were observed for a seven week period. Of the group receiving 30 mg/kg polymer at tumor resection all four were alive at 47 days without any evidence of tumor recurrence. Of the group receiving 65 mg/kg as a single dose at the time or resection, one died on day 16 after tumor recurrence while the other three were alive at 47 days without any evidence of tumor recurrence. Z

EXEMPLE 16

A second study of prevention of tumor recurrence was run in Fischer rats similar to that in Example 15 except that three polymers of different imide contents were used. Imide levels were zero, five and 21.7 percent. In this study trochar implantation of tumor was done as described in Examples 13, 14 and 15. Excision of all tumors was performed 14 days after implantation.

One group of four rats were used as controls and received no treatment t the time of excision. Tumor recurrence was 100% on days 21, 33, 40 and 44 post excision for an average recurrence time of 34 days. Of this control group two rats died on day 44 and two were alive and were sacrificed at that time. All four were found to have evidence of metastases.

A second group of five rats received a single I.P. dose of 30 mg/kg of the polymer from Example 2a (zero percent imide) at the time of tumor resection. Of this group tumor recurred in two rats on day 33 post resection and in a third on day 40. After 55 days 3 of 5 rats (60%) had tumor recurrence. A third group of six rats received a single I.P. dose of 30 mg/kg of the polymer from Example 3, Table IV-1, containing 5 percent imide functionality, at the time of tumor resection. No tumor recurrence was observed in any animal throughout 55 days. On day 55 two of these rats died (without tumor)

and upon examination no evidence of metastases was found.

A fourth group of six rats received a single I.P. dose of 30 mg/kg of the polymer from Example 7, Table VI-A, containing 21.7 percent imide, at the time of tumor resection. In this group one animal had tumor recurrence at day 21 and a second on day 43. All were alive after 55 days. Thus only 2 of 6 recurred for an average of 33%.

EXAMPLE 17

Animal experiments described in Examples 13 through 16 utilized polymers dosed by injection into the peritoneal cavity. This example illustrates the utility of an imide containing composition when administered orally at the time of tumor resection to prevent or retard tumor recurrence. In Example 16 it was noted that control animals receiving no drug at the time of tumor resection showed an average time for tumor recurrence of 34 days.

In this example a group of 10 Fischer rats received trochar implantation of tumor as in Example 13. The developed tumors were surgically removed on day 13 following implantation and concurrently each rat was orally intubated with one ml. sterile water containing 30 mg/kg of the imide containing polymer of Example 7, Table VI-A (21.7 percent imide). Tumor recurrence was then observed over a 10 week period. One rat died at the time of surgical tumor removal. Of the remaining nine rats small tumor recurrences were observed in seven animals at days 42, 42, 42, 43, 46, 50 and 59 following tumor excision. Two rats were free of tumor recurrence after 70 days.

EXAMPLE 18

The purpose of this experiment was to determine if exposure of tumor cells to polymer from Example 7-VI-A altered their antigenicity and/or had a direct cytotoxic effect on the tumor cells.

Tumor cells were prepared from the BLCa tumor described in Example 13 by excising a subcutaneous tumor mass. The cells were then brought into suspension by teasing the cells out of the tumor with additional gentle trypsinization of the tumor pieces. The separated cells were washed three times in balanced salt solution (BSS) and counted to determine living/dead ratio. A 90–95 percent cell population was obtained at this point.

Tumor cells at a concentration of $1 \times 10^5$ cells per ml., in Eagles minimal essential media in Earl's BSS, plus 10% fetal calf serum were incubated with 30 mg/ml of polymer from Example 7-VI-A. Incubation was performed at 37° C. for 90 minutes following which the cells were brought out of suspension by centrifugation at 300 g for six minutes. The cells were again examined for viability which had not changed from the pre-incubation level. The procedure was repeated on three separate occasions.

Cells from this experiment were injected into male Fischer rats subcutaneously at a dose of $1 \times 10^6$ cells. Five animals were injected with polymer treated cells and compared to five animals who received tumor cells treated as above but without added polymer. The results are summarized in Table XII.

TABLE XII

| Rat No. | Controls[1] Days to develop 2–3 cm tumor | Test Animals Days to Develop 2–3 cm tumor |
|---|---|---|
| 1 | 11 | 11 |
| 2 | 11 | 11 |
| 3 | 13 | 13 |
| 4 | 11 | 11 |
| 5 | 13 | 11 |

[1] $1 \times 10^6$ Tumor cells not incubated with polymer, inoculated S.C.
[2] $1 \times 10^6$ Tumor cells preincubated with polymer from Example 7-VI-A, inoculated S.C.

There was no difference between these animals in the time of tumor development. Further, the growth pattern of the tumor subsequent to this was comparable between the two groups. The conclusion from these experiments is that at the dose utilized, polymer from Example 7-Table VI-A (21.7% imide) did not have a direct cytotoxic effect on BLCa tumor cells. Additionally, preincubation of polymer with the tumor cell did not alter the antienicity of the tumor cells.

EXAMPLE 19

The direct toxicity of imide containing polymer from Example 7-VI-A was determined on normal male Fischer rats. Both I.P. and I.V. injection of polymer consisted of approximately 1 ml of physiological saline containing the appropriate quantity of polymer. To determine toxicity, polymer at doses of 100 mg/kg with increasing increments of 100 mg/kg up to 1000 mg/kg were given to five animals in each dose group. Polymer was administered both intraperitoneally and intravenously. No toxicity or animal deaths were observed with animals utilizing the intraperitoneal route up to 30 days of observation on a total of 50 rats. Toxicity was, however, observed when polymer was given in doses of 800 mg/kg (I.V. route) and over. One out of five animals at 800 mg/kg, two out of five animals at 900 mg/kg and four out of five animals at 1000 mg/kg appeared to develop convulsions upon intravenous administration of polymer and died. No toxicity or deaths were noted in animals given I.V. doses of 700 mg/kg or less over the 30 day observation period (35 animals).

After the 30 day observation period the 85 surviving rats were sacrificed and the brain, lung, heart, liver, kidney and spleen from each rat subjected to gross and microscopic pathology. No drug associated abnormalities were observed in any of the organ tissues.

In another study the toxicity of the above polymer administered I.P. was compared to that administered orally. The polymer from Example 7-VI-A was administered at doses of 100 mg/kg, 500 mg/kg and 1000 mg/kg either by injection (i.P.) or by gavage (P.O.) to each of five Fischer rats per dose group. The rats were observed for 14 days and no deaths or toxic manifestation occurred. After 14 days all animals were sacrificed, both from I.P. and P.O. drug administration, and the brain, lung, heart, liver, kidney and spleen from each animal subjected to gross and microscopic pathology. Again no absnormalities were observed in any of the organ tissues.

EXAMPLE 20

Polymers of the invention as described in Examples 3 and 4 were evaluated in normal Lewis rats for their ability to stimulate immune responses in terms of increasing 19-S (IgM) antibody producing cells to heterologous erythrocytes (Sheep Red Blood Cells, SRBC) by the standard Jerne Plaque assay method. See: "Textbook of Immunology", J. T. Barrett, C. V. Mosby Company, 1978 and "Immunology", H. N. Eisen, Medical Department, Harper and Row Publishers Inc., 1974. In a typical test an animal, in this case Lewis rats, is immunized with one ml of a 1:5 dilution of washed SRBC in physiological saline via the tail vein. At the same time the animals are given I.P. injections of the indicated polymer in one ml physiological saline. After 4 days spleen cells from the immunized animals are plated in an agarose tissue culture system with SRBC. The tissue culture medium supports the growth and excretion of antibody by the antibody-synthesizing cells. These antibodies diffuse from the originating cell and attach to neighboring erythrocytes. Serum compliment (normal guinea pig serum) is added promoting lysis of the RBC that have become coated with antibody forming a clear area, or plaque, around the antibody-forming cell. Such plaques (PFC) are counted and expressed as numbers of PFC per $1 \times 10^6$ spleen cells. The results are summarized in Table XIII. All polymer compositions in Table XIII were tested at 30 mg/kg.

TABLE XIII

| Polymer Source from Example No. | Percent Imide from IR Imide/Amide ratio | Total Animals in Average | IgM PFC/ $1 \times 10^6$ Spleen Cells | Stimulation Index Control = 1.00 |
|---|---|---|---|---|
| None (Control) | — | 16 | 568 | 1.00 |
| 2a | 0 | 10 | 1564 | 2.75 |
| 3-IV-1 | 5.3 | 6 | 1446 | 2.54 |
| 4 | 6.5 | 6 | 1478 | 2.60 |
| 3-IV-3 | 11.5 | 10 | 1620 | 2.86 |
| 3-IV-4 | 16.5 | 10 | 1770 | 3.12 |
| — | 16.0 | 6 | 1866 | 3.28 |
| 3-IV-6 | 24.1 | 10 | 1968 | 3.46 |
| — | 24.4 | 6 | 1984 | 3.49 |
| 3-IV-7 | 28.2 | 10 | 1992 | 3.51 |
| — | 32.6 | 6 | 1268 | 2.23 |
| 3-IV-8 | 34.7 | 10 | 1664 | 2.93 |
| 3-IV-9 | 50.1 | 10 | 926 | 1.63 |

Lewis rats with polymer given either I.P. or orally and (2) in Lewis rats as a replacement for thymic function, again with polymer given either I.P. or orally. In case (1) the procedure followed that of Example 20. In case (2) normal thymic function was removed by adult thymectomy (Tx) which was surgically performed at the age of 8 to 12 weeks and high doses of total body irradiation (TBI) followed by bone marrow cell repopulation (BM). Thymectomy, total body irradiation and bone marrow cell repopulation were all done by standard procedures described by Falk, R. E. et al, *Surgery*, October (1978), by Falk, R. E. et al., Abstract, *Canadian Society for Clinical Investigation*, Jan. 24–17, 1978, Vancouver and by Falk, R. E. et al., Abstract, *Royal College of Physicians and Surgeons*, Jan. 25–28, 1978, Vancouver.

In these procedures TBI and BM repopulation were done the day following surgical thymectomy. For TBI the animals were irradiated using a [137] cesium source (Atomic Energy of Canada). The dose of radiation in this machine is calibrated by the supplier and is applied in an equitable fashion over the entire body surface of animals placed in the container. For BM repopulation, single cell suspensions of bone marrow cells were prepared by washing the long bones of the femur and tibia in the rat with a balanced salt solution (BSS) at 4° C. The cells were washed three times in BSS and counted in a haemocytometer to determine viability and the appropriate cell dilution. Cells were administered I.V. using preparations with greater than 90% viability. To each rat BM repopulation involved $1 \times 10^8$ cells.

The mortality rate of animals for the total Tx+TBI+Bm procedure was less than 10%. These animals were then allowed to recover for a period of 6 weeks prior to running the IgM antibody response to SRBC.

After the recovery period the polymer of Example 7-Table VI-A and the SRBC were administered as in Example 20. The results of the overall experiment are shown in Table XIII-A.

TABLE XIII-A

IgM Antibody REsponse of Lewis Rats

| Polymer | Animal Treatment | Number of Animals | Dose mg/kg Route | Mean Response IgM~ PFC/1 × $10^6$ Spleen Cells | Stimulation Index Control = 1.00 |
|---|---|---|---|---|---|
| None | Normal Untreated Controls | 10 | — | 174.2 | — |
| Example 7-Table VI-A | Normal | 10 | 30*/I.P. | 836.0 | 4.78 |
| Example 7-Table VI-A | Normal | 10 | 30*/oral | 865.6 | 4.96 |
| None | Tx, 950R, BM Controls** | 10 | — | 73.6 | — |
| Example 7-Table VI-A | Tx, 950R, BM | 10 | 30*/I.P. | 740.4 | 10.10 |
| Exaample 7-Table VI-A | Tx, 950R, BM | 10 | 30*/oral | 474.0 | 6.42 |

*Similar results were obtained with 15 mg/kg.
**Tx = Thymectomy.
R = Rads of total body irradiation.
BM = Bone marrow reconstituted.

EXAMPLE 20-A

In a further set of experiments the effects of polymer from Example 7-Table VI-A on IgM antibody response to SRBC antigen (again using the Jerne Plaque assay method as in Example 20) were evaluated (1) in normal

EXAMPLE 21

Nine polymers of varying imide content (0 through 35 percent) and identical to many of those described in Example 20, Table XIII, were evaluated in Fischer rats for their comparable performance as a function of percent imide in preventing recurrence of primary BLCa tumor after tumor resection. The experimental procedure follows that described in Examples 15, 16 and 17 except that in this case 10 rats were used for all dose groups and controls and the various imide compositions were dosed both at 30 mg/kg and 15 mg/kg by I.P. injection in 1 ml saline. Controls received 1 ml saline I.P. only. One 10 animal group was given 30 mg/kg orally of polymer from Example 7-VI-A (21.7% imide) as noted. All tumors were surgically removed eleven days after trochar implantation and drugs were administered in single doses as above on day one after tumor excision. The results are summarized in Table XIV. Of interest is that the average days for tumor recurrence for the 10 controls was 32.3 comparing well with the control average of 34 days (4 rats) in Example 16.

TABLE XIV

| No. | Polymer Source Example | Percent Imide | Dose* mg/kg | X=1 | 2 | 3 | 4 | 5 | 6 | 7 | 8 | 9 | 10 |
|---|---|---|---|---|---|---|---|---|---|---|---|---|---|
| 1. | Control | — | — | 0 | 1 | 2 | 3 | 5 | 10 | — | — | — | — |
| 2. | 2a | 0 | 30 | 0 | 0 | 2 | 3 | 3 | 3 | 3 | 4 | 4 | 5 |
|   |   |   | 15 | 0 | 0 | 2 | 3 | 5 | 5 | 5 | 6 | 6 | 7 |
| 3. | 3-IV-1 | 5.3 | 30 | 0 | 0 | 0 | 0 | 0 | 1 | 1 | 1 | 2 | 3 |
|   |   |   | 15 | 0 | 0 | 2 | 2 | 2 | 2 | 2 | 2 | 2 | 3 |
| 4. | 4 | 6.5 | 30 | 0 | 0 | 0 | 0 | 0 | 0 | 0 | 0 | 1 | 2 |
|   |   |   | 15 | 0 | 0 | 0 | 1 | 2 | 3 | 3 | 3 | 5 | 5 |
| 5. | 3-IV-4 | 16.5 | 30 | 0 | 0 | 0 | 0 | 0 | 0 | 0 | 0 | 0 | 0 |
|   |   |   | 15 | 0 | 0 | 0 | 1 | 2 | 2 | 2 | 2 | 2 | 3 |
| 6.* | 7-VI-A | 21.7 | 30 | 0 | 0 | 0 | 0 | 0 | 0 | 1 | 2 | 4 | 4 |
| 7. | 3-IV-6 | 24.1 | 30 | 0 | 0 | 0 | 0 | 1 | 1 | 1 | 1 | 1 | 1 |
|   |   |   | 15 | 0 | 0 | 0 | 0 | 0 | 1 | 1 | 2 | 2 | 2 |
| 8. | — | 24.4 | 30 | 0 | 0 | 0 | 0 | 0 | 0 | 0 | 0 | 1 | 3 |
|   |   |   | 15 | 0 | 0 | 0 | 1 | 3 | 5 | 5 | 6 | 6 | 6 |
| 9. | 3-IV-7 | 28.2 | 30 | 0 | 0 | 1 | 3 | 5 | 5 | 5 | 5 | 6 | 6 |
|   |   |   | 15 | 0 | 0 | 0 | 1 | 2 | 3 | 3 | 4 | 6 | 7 |
| 10. | 3-IV-8 | 34.7 | 30 | 0 | 0 | 0 | 2 | 2 | 3 | 3 | 3 | 3 | 4 |
|   |   |   | 15 | 0 | 0 | 1 | 1 | 2 | 3 | 3 | 3 | 3 | 4 |

*Example No. 6 given orally, all others I.P. All groups of 10 rats per dose.

EXAMPLE 22

The 100% imide of EMA (sp. visc.=0.66) from Example 5-A evaluated for tumor growth inhibition at an independent testing laboratory using the following procedure.

Solid Sarcoma 180 was implanted by trocar (2 mm diameter) into the flask of male swiss mice. The polymer from Example 5-A was administered by I.P. injection at the dosage indicated in 0.5 ml saline on six consecutive days starting with day one after tumor implantation. Groups of 5 mice received 25,50 and 100 mg/kg dose as described. Higher doses; 200, 400 and 800 mg/kg proved to be toxic as indicated. On the day following the last I.P. drug injection the animals were sacrificed and the tumor removed by dissection and weighed. Tumor inhibition was calculated as percent of treated animal tumor weights divided by control animal tumor weights. Results are shown in Table XV indicating no activity exhibited by the EMA full 100% imide.

TABLE XV

| Drug Dose mg/kg[1] | Mice Start | Mice End | Initial Avg. wt. g. | Final Avg. wt. g. | Average Excised Tumor wt mg. | Inhibition Test/ controls in % |
|---|---|---|---|---|---|---|
| 25 | 5 | 5 | 27.0 | 31.4 | 1074.4 | −9 |
| control | 5 | 5 | 27.6 | 32.2 | 985.4 | — |
| 50 | 5 | 5 | 26.8 | 34.0 | 724.4 | +26 |
| control | 5 | 5 | 27.6 | 32.2 | 985.4 | — |
| 100 | 5 | 5 | 26.8 | 31.0 | 587.6 | −16 |

TABLE XV-continued

| Drug Dose mg/kg[1] | Mice Start | Mice End | Initial Avg. wt. g. | Final Avg. wt. g. | Average Excised Tumor wt mg. | Inhibition Test/ controls in % |
|---|---|---|---|---|---|---|
| control | 5 | 5 | 29.0 | 32.3 | 505.8 | — |
| 200 | 5 | 2 | 60% of animals died. | | | NC[2] |
| control | 5 | 5 | 29.0 | 32.3 | 505.8 | — |
| 400 | 5 | 3 | 40% of animals died | | | NC[2] |
| control | 5 | 5 | 27.6 | 32.2 | 985.4 | — |
| 800 | 5 | 0 | 100% of animals died | | | — |
| control | 5 | 5 | 27.6 | — | — | — |

[1]Swiss male mice, S-180 by trocar SC, dose given on 6 consecutive days I.P. in 0.5 ml saline following tumor implantation. Animals sacrificed on day following last drug injection.
[2]Not calculated because of acute toxicity.

EXAMPLE 23

A preferred polymer of the invention was evaluated in normal male Lewis rats for possible activity in increasing the numbers of peritoneal macrophage and their activity to phagocytize polystyrene latex particles which has been demonostrated for a number of immune system modulators such as Bacillus Calmette-Guerin (BCG), pyran copolymer, and other such agents.

Four groups of six young adult (2–4 months old) normal male Lewis rats were administered drug or saline (controls) as follows. Group-1 received 1 ml of saline given I.P.; Group-2 received the polymer of Example 7-Table VI-A at 30 mg/kg in 1 ml of saline given I.P.; Group-3 received the polymer of Example 7-Table VI-A at 30 mg/kg in 1 ml of saline given orally and Group-4 received 0.1 mg of BCG in 1 ml of saline given I.P.

On days 1, 3 and 5 following the above administration two of each of the four above groups were sacrificed and the peritoneal cavity cells were harvested. Harvesting involved the following procedure. 100 ml of chilled RPMI 1640 media was injected I.P. and after gentle massage the total peritoneal fluid was drained and the cells from each single peritoneal cavity were separated by spinning at 1000 r.p.m. These cells were stained with NSE (non specific esterase) stain and washed three times with chilled (4° C.) media. Finally the cells from each single cavity were suspended in 10 ml of media and counted to obtain the average number of cells consisting of 80–95% macrophage obtained from each peritoneal cavity as a function of the above treatment group type and time (days) after treatment.

The Latex particle phagocytosis activity of each set of peritoneal cavity cells was determined as follows. A suspension of the above cells was prepared in a concentration of 40–50 million cells per ml of 50% Fetal Calf serum plus RPMI media in a 5 ml tube. To the suspension was added 100 lamda of polystyrene latex (10% solids, particle diameter=one micron, Dow Diagnostics, Indianapolis, Indiana) and the mixture was incubated for 1 hr at 37° C. The cells were then spun down, washed 3 times with RPMI media and finally resuspended in 0.5 ml saline. Slides of the cell suspensions were prepared and microscopically examined to determine the extent of latex particle phagocytosis into the macrophage cell. Those cells which contained 10 or more latex particles were considered positive and the total number of such cells (those containing 10 or more latex particles) expressed as percent of the total number of cells in the suspension.

The data of these experiments are shown in Table XVI for duplicate experiments.

The data in Table XVI show conclusively that the preferred polymer of the invention does not increase peritoneal macrophage over control values when administered either I.P. or orally and further the latex phagocytosis activity of such peritoneal macrophage is not increased over normal macrophage activity. By contrast other immune system modulators, as shown by data on BCG, greatly increase the number of peritoneal macrophage and such macrophage have greatly increased latex phagocytosis activity. This high activity decreases to normal values after 3 days and beyond.

In contrast to the above results which indicate that the polymers of this invention do not activate macrophage function, the results in Examples 20 and 20A show that these polymers nevertheless act as B-cell modulators in normal animals and stimulate B-cell antibody response when given either I.P. or orally. Further, this effect is noted even in the absence of thymic function, which indicates that the polymers of the invention act as thymic function replacement in the activation of B-cells for increased antibody production.

TABLE XVI

Peritoneal Macrophage Number and Activity when Treated as described in Example 23

| Day Sacrificed following drug | Treatment | Experiment 1 | | Experiment 2 | |
|---|---|---|---|---|---|
| | | No. of cells per each cavity (×10⁶) | Latex Uptake % of cells with over 10, latex particles | No. of cells per each cavity (×10⁶) | Latex Uptake % of cells with over 10 latex particles |
| 1 | Control (1.0 ml Saline) | 10 | 25 | 3 | 29 |
| | | 18 | 31 | 3 | 21 |
| | Ex 7-VI-A, 30 mg/kg, I/P.* | 5 | 27 | 11 | 30 |
| | | 9 | 27 | 13 | 25 |
| | EX 7-VI-A, 30 mg/kg, Oral* | 7 | 27 | 4 | 20 |
| | | 6 | 31 | 6 | 15 |
| | BCG, 0.1 mg, I.P. | 27 | 97 | 26 | 90 |
| | | 33 | 97 | 28 | 84 |
| 3 | Control (1.0 ml saline) | 5 | 8 | 5 | 20 |
| | | 6 | 11 | 4 | 15 |
| | EX 7-VI-A, 30 mg/kg, I.P.* | 3 | 11 | 8 | 30 |
| | | 6 | 8 | 8 | 15 |
| | Ex 7-VI-A, 30 mg/kg, Oral* | 5 | 20 | 8 | 11 |
| | | 5 | 8 | 6 | 10 |
| | BCG, 0.1 mg, I.P. | 4 | 9 | 6 | 25 |
| | | 8 | 13 | 15 | 32 |
| 5 | Control (1.0 ml saline) | 3 | 26 | 1 | 16 |
| | | 2 | 23 | 1 | 7 |
| | Ex 7-VI-A, 30 mg/kg, I.P.* | 5 | 45 | 5 | 12 |
| | | 6 | 37 | 3 | 10 |
| | EX 7-VI-A, 30 mg/kg, oral* | 2 | 45 | 1 | 15 |
| | | 13 | 37 | 1 | 11 |
| | BCG, 0.1 mg, I.P. | 3 | 26 | 2 | 20 |
| | | 6 | 38 | 7 | 25 |

*Lymphocyte-type cells were extracted from the spleen, thymus, lymph nodes and bone marrow of all of the animals treated with polymer from Ex. 7-VI-A and in no case was any latex phagocytosis activity noted as being any greater than for similar cells obtained from the control rats.

Various other examples as will further illustrate the invention can be carried out by substitution of other substantially equivalent materials for the specific materials recited in the foregoing examples.

Thus, propylene can be substituted for an equivalent amount of ethylene in the foregoing examples as illustrative of the defined olefin monomers with substantially similar results.

So also, citraconic anhydride can be substituted for an equivalent amount of maleic anhydride in the foregoing examples as illustrative of the defined polycarboxylic anhydrides with substantially similar results.

Polymers of still lower average molecular weight can be prepared by solvent-nonsolvent fractionation of the EMA polymer prepared in Example 1, above. This lower molecular weight polymer can then be substituted for an equivalent amount of the polymer of Example 1 in the foregoing examples with substantially similar results.

Other pharmaceutically acceptable salts of imides of the invention can be made by converting the ammonium salt derivatives to salts such as, for example, sodium and potassium. For example, the ammonium salt derivative of Example 3, Table IV, Run 4, above, can be converted to the half-amide, half free carboxyl derivative by passage of a 5% aqueous solution of the ammonium salt through a weak base cation exchange column, for example, Amberlite IRC-84 (crosslinked acrylic copolymer, Rohm and Haas Company). The resulting solution in the free carboxyl form can then be neutralized with either NaOH or KOH, respectively, and the neutralized solution freeze dried to obtain the corresponding sodium and potassium salt derivatives.

The low molecular weight EMA polymer of Example 1, above, also can be converted into the half-monomethyl secondary amine, half-monomethyl amine carboxylate salt by the procedure of Example 2 (a) by reacting the solution of EMA and acetone with a solution of methylamine in acetone instead of ammonia in acetone. The product can then be refluxed in xylene to obtain a partial N-methyl substituted imide derivative which has an imide function as well as the presence of secondary methyl amide, ionized COO$^-$ and amine carboxylate functions.

Still other examples can be prepared as will be readily apparent to the person skilled in the art after reading the present disclosure without departing from the spirit and scope of the invention. It shall be understood that all such further examples are included within the scope of the appended claims.

What is claimed is:

1. A composition selected from the group consisting of a copolymer of at least one olefin monomer having from 2 to about 4 carbon atoms and at least one α,β-unsaturated polycarboxylic anhydride having from 4 to about 6 carbon atoms, having an average molecular weight of from about 300 to about 1500, and derivatized to obtain both (a) half-amide, half-carboxyl acid groups and (b) imide groups in with said imide groups comprise from about 5% by weight to about 40% by weight of said derivatized groups, and the N-alkylated derivatives and pharmaceutically acceptable cationic salt derivatives of said derivatized copolymer, said N-alkylated derivatives having from 1 to 4 carbon atoms in the alkyl substituents.

2. The composition of claim 1 in which the olefin monomer is ethylene.

3. The composition of claim 1 in which the polycarboxylic anhydride is maleic anhydride.

4. The composition of claim 1 in which the olefin monomer is ethylene and the polycarboxylic anhydride is maleic anhydride.

5. The composition of claim 4 in which the average molecular weight is about 850.

6. The composition of claim 1 in which the half-amide, half-carboxyl acid group is derivatized to the half-amide, half-ammonium salt group and the half-amide and imide are unsubstituted.

7. The composition of claim 5 in which the half-amide, half-carboxyl acid group is derivatized to the half-amide, half-ammonium salt group and the half-amide and imide are unsubstituted.

8. The composition of claim 1 in which the imide group comprises from about 10% to about 25% of said derivatized groups.

9. The composition of claim 5 in which the imide group comprises from about 10% to about 25% of said derivatized groups.

10. The composition of claim 9 in which the imide group comprises about 20% of said derivatized groups.

11. The composition of claim 10 in which the half-amide, half-carboxyl acid group is derivatized to the half-amide, half-ammonium salt group and the half-amide and imide are unsubstituted.

* * * * *

UNITED STATES PATENT AND TRADEMARK OFFICE
CERTIFICATE OF CORRECTION

PATENT NO. : 4,255,537

DATED : March 10, 1981

INVENTOR(S) : Joseph E. Fields, Samuel S. Asculai & John H. Johnson

It is certified that error appears in the above—identified patent and that said Letters Patent is hereby corrected as shown below:

In col. 3, line 57, "half-imide" should read --half-amide--.
In col. 11, line 42, "900 ml" should read --900 ml water--.
In col. 12, line 23, "Example 2" should read --Example 2a--.
In col. 17, line 16, "$CO_3^-$" should read --$CO_2^-$--.
In col. 21, line 59, "or" should read --and--.
In col. 26, line 52, "t" should read --at--. In col. 28, line 2, after "Test Animals" insert --(2)--. In col. 31, line 46, "flask" should read --flank--. In col. 35, line 28 (in Claim 1) "obtain" should read --contain--.

Signed and Sealed this

Seventh Day of July 1981

[SEAL]

Attest:

RENE D. TEGTMEYER

Attesting Officer

Acting Commissioner of Patents and Trademarks